United States Patent
Ebert et al.

(10) Patent No.: US 8,614,091 B2
(45) Date of Patent: Dec. 24, 2013

(54) PNMT AS A NOVEL MARKER FOR PROGENITOR CELLS

(76) Inventors: Steven N. Ebert, Chuluota, FL (US); Karl Pfeifer, Bethesda, MD (US)

( * ) Notice: Subject to any disclaimer, the term of this patent is extended or adjusted under 35 U.S.C. 154(b) by 0 days.

(21) Appl. No.: 13/229,236

(22) Filed: Sep. 9, 2011

(65) Prior Publication Data

US 2012/0183528 A1 Jul. 19, 2012

Related U.S. Application Data

(63) Continuation of application No. 11/918,678, filed as application No. PCT/US2005/010611 on Mar. 31, 2005, now abandoned.

(60) Provisional application No. 60/562,931, filed on Apr. 16, 2004, provisional application No. 60/558,146, filed on Apr. 1, 2004, provisional application No. 60/557,785, filed on Mar. 31, 2004.

(51) Int. Cl.
*C12N 5/00* (2006.01)
*A01N 63/00* (2006.01)

(52) U.S. Cl.
USPC ........................................ 435/325; 424/93.1

(58) Field of Classification Search
USPC ........................................ 435/325; 424/93.1
See application file for complete search history.

(56) References Cited

FOREIGN PATENT DOCUMENTS

WO    WO 03035838    5/2003
WO    WO03/054202   *  7/2003

OTHER PUBLICATIONS

Beltrami et al. (Cell, 114(6):763-76,2003).
Ebert et al. (Circ. Res 88, 117-124, 2001).
Claycomb et al. (JBC, 251(19):6082-9, 1976).
Huang et al. (J Clin Invest, 98(6):1298-1303, 1996).
Quaife et al. (Transgenic Res, 33:388-400, 1994).
Soriano et al. (Nature Genetics, 21:70-71, 1999).
O'Gorman et al. (PNAS, 94:14602-14607, 1997).
Xiang et al. (Development, 127:1607-1616, 2000).
Ebert et al. (J Mol Cell Cardiol 28, 1653-1658, 1996).

* cited by examiner

*Primary Examiner* — Gerald G Leffers, Jr.
*Assistant Examiner* — Magdalene Sgagias
(74) *Attorney, Agent, or Firm* — Timothy H. Van Dyke; Beusse, Wolter, Sanks, Mora & Maire, P.A.

(57) ABSTRACT

In certain aspects, the present invention provides methods and compositions relating to a Pnmt-positive progenitor cell. In certain aspects, the present invention relates to methods for isolating and transplanting the subject progenitor cells, and methods for treating diseases such as myocardiac injuries and neurodegenerative disorders.

5 Claims, 12 Drawing Sheets

PNMT AS A NOVEL MARKER FOR PROGENITOR CELLS

RELATED APPLICATIONS

This application is a continuation of U.S. Ser. No. 11/918,678 filed Nov. 21, 2008 now abandoned which claims priority to PCT/US2005/010611 filed Mar. 31, 2005 which claims the benefit of the filing dates of U.S. Provisional Application No. 60/557,785, filed Mar. 31, 2004; U.S. Provisional Application No. 60/558,146, filed Apr. 1, 2004; and U.S. Provisional Application No. 60/562,931, filed Apr. 16, 2004. The entire teachings of the referenced Provisional Applications are incorporated herein by reference in their entirety.

FUNDING

Work described herein was funded, in whole or in part, by funds from the National Institute of Child Health Development (NICHD). The United States government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 22, 2011, is named 1669107C.txt and is 1,126 bytes in size.

FUNDING

Work described herein was funded, in whole or in part, by funds from the National Institute of Child Health and Human Development (NICHD). The United States government has certain rights in the invention.

BACKGROUND OF THE INVENTION

Cure of a wide variety of diseases or tissue injuries by specific replacement of damaged or malfunctional tissues by use of totipotent, pluripotent or multipotent stem cells is on the horizon in clinical practice (see, e.g., Fuchs, et al., 2000, Cell, 100:143-156; Weissman et al., 2000, Cell, 100:157-168; Blau, et al., 2001, Cell, 105:829-841). To transmute a somatic cell into the variety of cell types needed for tissue regeneration and reconstruction in vertebrates is a realistic goal. In fact, tissues that were formerly considered incapable of extensive regeneration, such as brain, spinal cord, and cardiac muscle, now appear to be capable of reconstruction functionally, at least to some extent, by stem cell populations. Stem cells derived from the embryo and from adult tissues have been shown to have extensive potentials for self-renewal and differentiation.

Therefore, there is a need to develop methods of identifying or isolating stem cells for tissue reconstruction procedures. Investigation in these areas may lead to realistic approaches in the future for stem cell therapy in a variety of human diseases, tissue injuries, and other clinical problems.

SUMMARY OF THE INVENTION

In certain embodiments, the present invention provides an isolated progenitor cell that expresses phenylethanolamine n-methyltransferase (Pnmt), referred to herein as a "Pnmt-positive" progenitor cell, including a mammalian progenitor cell (e.g., human or mouse). The Pnmt-positive progenitor cells can be isolated from various pluripotent stem cell cultures (e.g., adult bone marrow-derived stem cells, adipose-derived stem cells, cardiac-derived stem cells, neural-derived stem cells, embryonic stem cells, etc.), or from developing (e.g., embryonic) or adult tissue/organs. In certain cases, the subject progenitor cells differentiate into adrenergic cells. In certain other cases, the Pnmt-positive progenitor cells transiently differentiate into adrenergic-like cells, followed by further differentiation into cardiomyocytes, neuronal, and/or other specialized cell types.

In one specific embodiment, the Pnmt-positive progenitor cell is a cardiac progenitor cell (also referred to as cardiomyocyte progenitor cell). The Pnmt-positive cardiac progenitor cell may be also positive for other markers, such as c-kit, Sca-1, and MDR1. In certain embodiments, the progenitor cells differentiate into a cardiomyocyte in vivo, in vitro or ex vivo. Examples of cardiomyocytes include, but are not limited to, a pacemaker cell, such as a sinoatrial node (SAN) cell or an atrioventricular node (AVN) cell; a His bundle (HIS) cell; a Purkinje fiber (PUR) cell; an atrial working myocyte; and a ventricular working myocyte. The Pnmt-positive progenitor cell can be isolated, for example, from stem cell cultures or from developing hearts or adult hearts.

In another specific embodiment, the Pnmt-positive progenitor cell is a neural progenitor cell. The Pnmt-positive neural progenitor cell may also be positive for other markers, such as nestin. In certain embodiments, the progenitor cells differentiate into a neuronal cell, such as a brainstem neuronal cell or a retinal neuronal cell. This Pnmt-positive progenitor cell can be isolated, for example, from stem cell cultures or from developing brains or adult brains.

In certain embodiments, the present invention provides a method for identifying a cardiac progenitor cell. In this method, Pnmt expression is detected within a cell. If the cell expresses Pnmt and differentiates into a cardiomyocyte, then the cell is identified as a cardiac progenitor cell. Examples of cardiomyocytes include, but are not limited to, a pacemaker cell, such as a sinoatrial node (SAN) cell or an atrioventricular node (AVN) cell; a His bundle (HIS) cell; a Purkinje fiber (PUR) cell; an atrial working myocyte; and a ventricular working myocyte. The cell may also be positive for other markers, such as c-kit, Sca-1, and MDR1. In certain cases, the cell is isolated from stem cell lines/cultures or from a mammalian tissue such as a developing or adult heart. In a specific embodiment, the cell used in this method comprises a marker gene located at one or more loci of the Pnmt gene. Thus, expression of the marker gene recapitulates expression of Pnmt. Cardiac progenitor cells can then be readily detected by fluorescence-activated cell sorting (FACS), which detects the marker expression. Useful markers include, but are not limited to, beta-galactosidase, luciferase, fluorescent proteins such as GFP (green), BFP (blue), RFP (red), YFP (yellow), CFP (cyan), and other suitable markers (e.g., a cell-surface protein such as a membrane receptor).

In certain embodiments, the present invention provides a method of inducing a Pnmt-positive cardiac progenitor cell to differentiate into a cardiomyocyte. In this method, the Pnmt-positive cardiac progenitor cell is treated with an effective amount of one or more agent that induces the progenitor cell to differentiate into a cardiomyocyte. Examples of cardiomyocytes include, but are not limited to, a pacemaker cell, such as a sinoatrial node (SAN) cell or an atrioventricular node (AVN) cell; a His bundle (HIS) cell; a Purkinje fiber (PUR) cell; an atrial working myocyte; and a ventricular working myocyte. The progenitor cell may also be positive for other markers, such as c-kit, Sca-1, and MDR1. In certain cases, the progenitor cell is isolated from stem cell lines/cultures or a mammalian tissue (e.g., human), such as a developing or adult heart. The agents used this method to induce differentiation include, but are not limited to, catecholamines (norepinephrine or epinephrine), growth factors, hormones, and extracellular matrix proteins.

In certain embodiments, the present invention provides a method of treating a patient having a myocardial injury. In this method, at least one (one or more) Pnmt-positive cardiac progenitor cell is obtained and transferred into the patient, wherein the progenitor cell differentiates into a cardiomyocyte. Typically, cells identified as Pnmt-positive cardiac progenitor cells are cultured under conditions that result in their propagation, in order to produce a sufficient number of cells for the desired purpose. Examples of cardiomyocytes include, but are not limited to, a pacemaker cell, such as a sinoatrial node (SAN) cell or an atrioventricular node (AVN) cell; a His bundle (HIS) cell; a Purkinje fiber (PUR) cell; an atrial working myocyte; and a ventricular working myocyte. The progenitor cell may also be positive for other markers, such as c-kit, Sca-1, and MDR1. In certain cases, the progenitor cell is isolated from stem cell lines/cultures or a mammalian tissue (e.g., human), such as a developing or adult heart. Specific examples of myocardial injuries include myocardial infarction, cardiomyopathy, and congenital heart disease. Preferably, the progenitor cell is transferred to a damaged cardiac region.

In a specific embodiment, the subject method further includes expanding the Pnmt-positive progenitor cell ex vivo before transferring progenitor cells into the patient.

In another specific embodiment, the subject method further includes treating the patient with an immunosuppressive agent, such as FK-506, cyclosporin or GAD65 antibodies. In certain embodiments, expression of at least one major histocompatibility (MHC) gene (e.g., class I MHC, class II MHC, or class I and II MHC) is inactivated in the Pnmt-positive progenitor cell.

In certain embodiments, the present invention provides a transplant graft comprising the subject Pnmt-positive progenitor cells. Preferably, the transplant graft does not cause graft versus host rejection when transplanted into an animal.

In certain embodiments, the present invention provides a method of assessing a Pnmt-positive cardiac progenitor cell for its ability to regenerate cardiac tissues in vivo. In this method, a Pnmt-positive cardiac progenitor cell is obtained and transferred into a subject in need thereof. Preferably, the transferred progenitor cell contains a marker (e.g., a fluorescent marker). Then, the transferred progenitor cell is monitored by methods, for example, magnetic resonance imaging (MRI) or bioluminescence imaging (BLI). Useful markers include, but are not limited to, beta-galactosidase, luciferase, fluorescent proteins such as GFP (green), BFP (blue), RFP (red), YFP (yellow), CFP (cyan), and other suitable markers (e.g., a cell-surface protein such as a membrane receptor).

In certain embodiments, the present invention is a cell comprising a marker gene located at one or more loci of a Pnmt gene. Optionally, at least one (one or two) copy of the Pnmt gene is deleted in the cell. Useful markers include, but are not limited to, beta-galactosidase, luciferase, fluorescent proteins such as GFP (green), BFP (blue), RFP (red), YFP (yellow), CFP (cyan), and other suitable markers (e.g., a cell-surface protein such as a membrane receptor). Preferably, the cell is a mammalian cell (e.g., human). In certain cases, the cell is a progenitor cell.

In certain embodiments, the present invention is a method of making the subject cell comprising a marker gene located at one or more loci of the Pnmt gene.

In certain embodiments, the present invention relates to a method of identifying a compound that increases expression of Pnmt in a cell such as a progenitor cell. In this method, a cell comprising a marker gene located at one or more loci of the Pnmt gene is contacted with a test compound. The expression level of the marker gene in the cell is determined. If the expression level of the marker gene is higher in the presence of the test compound than in the absence of the test compound, the test compound is a compound that increases expression of Pnmt. Optionally, the identified compound can also increase the level of epinephrine in a cell. In certain cases, the subject method further includes assessing the ability of the test compound to increase expression of Pnmt in vivo (e.g., in an animal).

In certain embodiments, the present invention provides a non-human transgenic animal whose genome comprises a marker gene located at one or more loci of the Pnmt gene. Optionally, at least one (one or two) copy of the Pnmt gene is deleted in the animal. Exemplary markers include, but are not limited to, beta-galactosidase, luciferase, fluorescent proteins such as GFP (green), BFP (blue), RFP (red), YFP (yellow), CFP (cyan), and other suitable markers (e.g., a cell-surface protein such as a membrane receptor). For example, the transgenic animal includes mouse, rat, and rabbit.

In certain embodiments, the present invention relates to use of the isolated Pnmt-positive progenitor cells (e.g., cardiac progenitor cells) for treating myocardial injury in a patient. Specific examples of myocardial injuries include myocardial infarction, cardiomyopathy, and congenital heart disease. The isolated progenitor cell is optionally transferred to a damaged cardiac region.

In certain embodiments, the present invention provides a method of delivering a scaffold graft in a target tissue, comprising: a) seeding Pnmt-positive progenitor cells onto a biocompatible scaffold, thereby forming a scaffold graft; and b) implanting the scaffold graft from (a) in direct contact with, or adjacent to, a target tissue for a sufficient time, wherein cells of the target tissue associate with the implanted scaffold graft, thereby to form new tissue.

DETAILED DESCRIPTION OF THE INVENTION

Figure 1:
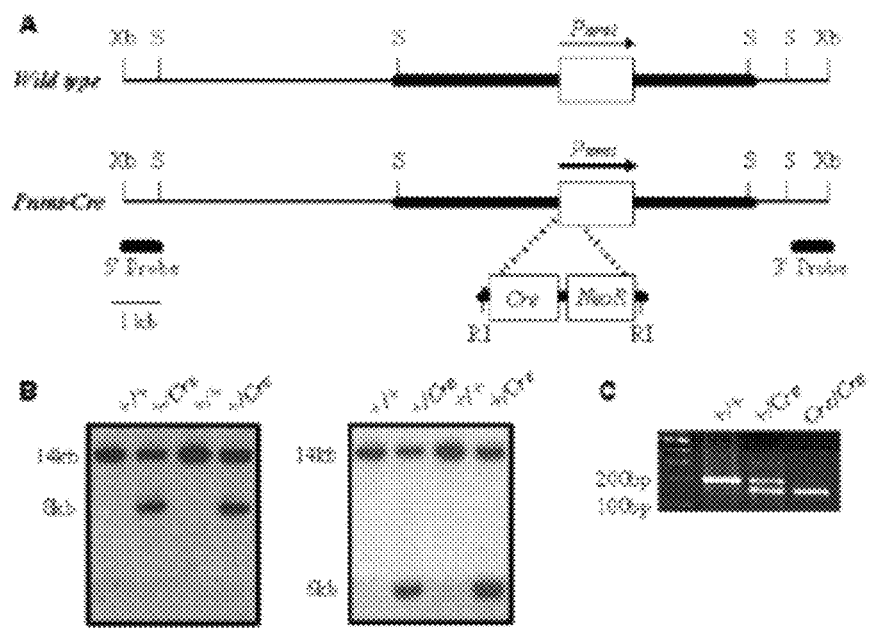
FIGS. 1A-1C show construction and verification of the Pnmt-Cre allele. (A) Cartoon depiction of the wild-type and Pnmt-Cre alleles. Sequences coding for the Pnmt RNA are depicted as an open rectangle with the direction of transcription indicated by the arrow. The thickened line shows the Pnmt sequences used to direct the homologous recombination event that introduces the Cre-recombinase gene (Cre) and the Neomycin resistance gene (NeoR) into Pnmt exon 1. Cre-recombinase is fused to the Pnmt 5' UTR sequences so that its transcription is entirely dependent upon Pnmt regulatory elements. The Cre insert contains transcriptional stop sequences. NeoR is driven by its own promoter and the NeoR gene is flanked with Frt sites to allow its removal via Flp recombinase. The 5' and 3' probes used for verifying the alleles are depicted. (B) Southern analysis of the mutated cell lines identifies clones carrying the Pnmt-Cre insertion allele. When digested with XbaI and EcoRI, correctly targeted cells display an 8 kb band (5' Probe/Left Panel) or a 6 kb band (3' probe/Right Panel) in addition to the 14 kb band indicative of the wild-type chromosome. (C) PCR analysis described in the Methods distinguishes homozygous wild type (+/+), heterozygous mutant (+/Cre), and homozygous mutant (Cre/Cre) animals. RI, EcoRI; S, SacI; Xb, XbaI.

The invention is based, at least in part, on Applicant's discovery that the epinephrine biosynthetic enzyme, phenylethanolamine n-methyltransferase (Pnmt), is a novel marker for cardiomyocyte progenitor cells in the developing heart. As described in the working examples, Applicant created a novel mouse model that enabled Applicant to follow the fate of intrinsic cardiac adrenergic (ICA) cells in the developing heart. This was accomplished through targeted insertion of the Cre-recombinase gene into the locus encoding for Pnmt, followed by crossing the resulting Pnmt-Cre mice with ROSA26 reporter (R26R) mice such that expression of LacZ (encoding β-galactosidase) was activated in cells that were selectively derived from the adrenergic lineage.

Pnmt is an enzyme that converts norepinephrine (NE) to epinephrine (EPI). EPI and NE are the major circulating catecholamines in most mammals. In adults, they are primarily produced in adrenergic neurons and adrenal chromaffin cells by the enzymatic conversion of the amino acid, L-tyrosine. The catecholamine biosynthetic pathway is shown below. The enzymes that catalyze each reaction are shown in italics above the arrows between precursors and products (TH, tyrosine hydroxylase; L-AAAD, L-aromatic amino acid decarboxylase; DBH, dopamine β-hydroxylase; PNMT, phenylethanolamine N-methyltransferase).
STR00001##

During periods of acute stress, EPI and NE are important modulators of "fight or flight" responses. Their actions induce significant metabolic and physiologic responses, especially in the cardiovascular system where they strongly increase cardiac output by stimulating both the rate and force of cardiac contractions. NE and/or EPI are also essential for fetal development because mice that lack the ability to produce these neurotransmitter hormones die from cardiovascular failure (Thomas et al., 1995, Nature 374:643-646).

In certain embodiments, the present invention relates to identification of a population of progenitor or stem cells that can be used in repair and/or regeneration of diseased or damaged tissue, such as the heart, brain, lungs, liver, kidney, adrenal glands, testes, retina, and possibly other cells/tissues/organs that have yet to be identified. Applicant's findings indicate that the Pnmt gene can be used as a specific marker to identify such progenitor/stem cells. These findings may significantly advance repair and regeneration studies by allowing isolation of the progenitor/stem cells easily and quickly by using Pnmt as a specific marker for this population of cells, which can then be used in a clinical setting to facilitate repair and regeneration of damaged tissue.

Pnmt-Positive Progenitor Cells

In certain embodiments, the present invention provides isolated Pnmt-positive mammalian progenitor cells. For example, Applicant identified a subclass of cardiac cells that have the functional and molecular characteristics of progenitor cells. In particular, these newly discovered cardiac progenitor cells are characterized by expression of Pnmt, and the ability to differentiate into cardiomyocytes. The present inventors also identified a subclass of Pnmt-positive neural cells that are neural progenitor cells.

In certain embodiments, the Pnmt-positive progenitor cells can be isolated from or derived from various stem cell cultures (e.g., adult bone marrow-derived stem cells, adipose-derived stem cells, cardiac-derived stem cells, neural-derived stem cells, embryonic stem cells, etc.). Alternatively, the Pnmt-positive progenitor cells can be isolated from developing (e.g., embryonic) or adult tissue/organs. In certain cases, the subject progenitor cells differentiate into adrenergic cells. In certain other cases, the subject progenitor cells (defined by their ability to express Pnmt) transiently differentiate into adrenergic-like cells followed by further differentiation into cardiomyocytes, neuronal, and/or other specialized cell types.

As used herein, the term "progenitor cell" or "precursor cell" refers to a cell that is derived from a stem cell by differentiation and is capable of further differentiation to more mature cell types. A "stem cell," as used herein, refers to a cell which is capable of essentially unlimited propagation either in vivo or ex vivo and differentiates to other cell types. Generally, stem cells can divide without limit. After division, the stem cell may remain as a stem cell, become a precursor cell or progenitor cell, or proceed to terminal differentiation. Although appearing morphologically unspecialized, the stem cell may be considered differentiated where the possibilities for further differentiation are limited.

As used herein, differentiation refers to the process whereby relatively unspecialized cells (e.g., stem cells or progenitor cells) acquire specialized structural and/or functional features characteristic of mature cells. Similarly, "differentiate" refers to this process. Typically, during differentiation, cellular structure alters and tissue-specific proteins appear.

In certain specific embodiments, the invention provides compositions or formulations comprising a Pnmt-positive progenitor cell and a physiologically compatible carrier. As used herein, "physiologically compatible carrier" refers to a physiologically acceptable diluent such as water and physiologically compatible buffers (e.g., phosphate buffered saline, Hank's solution, Ringer solution, or physiologically buffered saline).

In one embodiment, the invention provides Pnmt-positive progenitor cells for a variety of applications, including but not limited to, cellular replacement therapy for myocardial injuries and neurodegenerative disorders. The Pnmt-positive progenitor cells of the invention can also be used to carry out gene therapies in isograft, allograft or xenograft transplantations. As used herein, "allogeneic" refers to genetically different members of the same species; "isogeneic" refers to individuals of identical genetic constitution; and "xenogeneic" refers to members of a different species.

In another embodiment, the Pnmt-positive progenitor cells described herein can be used to produce recombinant cells, artificial tissues, and replacement organs in culture. They can also be used for the ex vivo production of catecholamines such as adrenaline (epinephrine). Molecular characteristics of the subject Pnmt-positive progenitor cells, such as cardiac progenitor cells, can be used in various diagnostic, pathological, or investigative procedures to identify, localize, and quantitate progenitor cells in tissues from a patient or experimental animal.

In certain embodiments, the present invention relates to methods of identifying Pnmt-positive progenitor cells, such as cardiac progenitor cells. Progenitor cells of the present invention can be identified by their expression of Pnmt (e.g., by FACS, immunocytochemical staining, RT-PCR, Southern Northern and Western blot analysis, and other such techniques of cellular identification as known to one skilled in the art).

For example, immunocytochemical staining can be carried out according to the following method. Heart tissues or cells are incubated with a primary antisera to the Pnmt protein. The antisera is rinsed off with PBS and incubated with the appropriate fluorescently labeled secondary antisera. Fluorescence microscopy is then performed to identify Pnmt-positive progenitor cells. Antisera useful according to the invention include monoclonal and polyclonal antibodies.

RT-PCR and Southern blot analysis are well known in the art. To illustrate, total cellular RNA prepared from heart tissues or cells is reverse-transcribed and amplified by PCR for about 35 cycles depending on the desired degree of amplification. The RNA samples are then either PCR-amplified with oligonucleotide primers for RT-PCR or probed with oligonucleotide probes for subsequent Southern blot hybridization. Sequences of the oligonucleotides are considered to be within the scope of the art. As a general guide, primers are selected from two different exons and encompass at least one intronic sequence of the Pnmt gene.

Methods of Isolation and Transplantation

In certain embodiments, the present invention relates to methods of isolating and transplanting Pnmt-positive progenitor cells, such as cardiac progenitor cells. As described above, the Pnmt-positive progenitor cells can be isolated from various pluripotent stem cell cultures (e.g., adult bone marrow-derived stem cells, adipose-derived stem cells, cardiac-derived stem cells, neural-derived stem cells, embryonic stem cells, etc.), or from developing (e.g., embryonic) or adult tissue/organs (e.g., heart). The isolated progenitor cells can then be expanded ex vivo and the resulting cells transplanted back into the donor as an isograft. In the donor, the transplanted Pnmt-positive progenitor cells may differentiate to provide, for examples, cardiomyocytes to replace cardiomyocytes such as those lost due to myocardial injury.

"Isolating" a progenitor cell refers to the process of removing a progenitor cell from a tissue sample and separating away other cells which are not progenitor cells of the tissue. An isolated progenitor cell is generally free from contamination by other cell types and generally has the capability of propagation and differentiation to produce mature cells of the tissue from which it was isolated. However, when dealing with a collection of progenitor cells, e.g., a culture of progenitor cells, it is understood that it is practically impossible to obtain a collection of progenitor cells which is 100% pure. Therefore, an isolated progenitor cell can exist in the presence of a fraction of other cell types which do not interfere with the utilization of the progenitor cell for analysis or production of other, differentiated cell types. Isolated progenitor cells are generally at least 30%, 40%, 50%, 60%, 70%, 80%, 85%, 90%, 95%, 98%, or 99% pure. Preferably, isolated progenitor cells according to the invention are at least 98% or at least 99% pure.

A progenitor cell is "expanded" when it is propagated in culture and gives rise by cell division to other progenitor cells. Expansion of progenitor cells may occur spontaneously as progenitor cells proliferate in a culture or it may require certain growth conditions, such as a minimum cell density, cell confluence on the culture vessel surface, or the addition of chemical factors such as growth factors, differentiation factors, or signaling factors.

A progenitor cell or differentiated cell is transplanted or introduced into a mammal when it is transferred, for example from a culture vessel into a subject (individual or patient). Transplantation, as used herein, can include the steps of isolating a progenitor cell according to the invention and transferring the progenitor cell into a subject Transplantation can involve transferring a progenitor cell into a subject by injection of a cell suspension into the subject, surgical implantation of a cell mass into a tissue or organ (e.g., heart) of the subject, or perfusion of a tissue or organ with a cell suspension. The route of transferring the progenitor cell or transplantation is determined by the need for the cell to reside in a particular tissue or organ and by the ability of the cell to find and be retained by the desired target tissue or organ. In the case where a transplanted cell is to reside in a particular location, it can be surgically placed into a tissue or organ or simply injected into the bloodstream if the cell has the capability to migrate to the desired target organ.

In certain embodiments, the present invention relates to methods of overcoming the problems of immune rejection resulting from transplantation of tissue. In one embodiment, the use of isografted progenitor cells makes it possible to alter the transplanted cells to render them or less likely to cause immune reaction. A further advantage of using progenitor cells, rather than an intact heart, is that transplanted progenitor cells can differentiate in situ and better adapt to the host environment. Another embodiment of the invention contemplates the use of partially differentiated progenitor cells ex vivo, for example, to form progenitor cells, which are subsequently transplanted into the host, with further differentiation taking place within the host.

In a specific embodiment, Pnmt-positive progenitor cells of the invention are immunologically blind or immunoprivileged. For example, immunoprivileged progenitor cells do not express sufficient amounts of class I and/or class II major histocompatibility (MHC) antigens (also referred to as HLA or human leukocyte antigen) to elicit an immune response from the host. Progenitor cells obtained from allogeneic or xenogeneic sources do not initiate a host versus graft response in immunocompetent transplant recipients.

As a non-limiting example, Pnmt-positive progenitor cells are isolated, cultured, and maintained in vitro. They can be obtained from tissue or from existing stem cell lines. Using genetic engineering techniques, the Pnmt-positive progenitor cells are engineered to express a reporter gene, such as enhanced green fluorescent protein (EGFP), beta-galactosidase gene, firefly luciferase gene, or other similar type of reporter, from the endogenous Pnmt locus. Differentiation of the progenitor cells is then initiated along pathways leading to the preferential development of specific cell and tissue types (e.g., cardiac, neural, renal, pulmonary or hepatic). Pnmt-linked reporter gene expression are used to isolate specific progenitor cells using fluorescence-activated cell sorting (FACS) or other methodology following induction of differentiation towards specific cell types in vitro. The Pnmt-positive cells are transplanted into or near damaged or diseased tissues. Targeted disruption of one or both Pnmt alleles does not appear to be detrimental, which is an advantage of using Pnmt as a marker. To avoid cell/tissue rejection, expression from the major histocompatibility (MHC) locus can be disrupted. Alternatively, the nuclear transfer technique can be employed to convert recipient progenitor cells into host cells by replacing the progenitor cell nuclei with nuclei isolated from the individual destined to receive the transplant. Typically, the nuclear transfer step is performed prior to engineering the progenitor cells to express a reporter gene from the Pnmt locus.

Methods of Molecular Imaging

In certain embodiments, the present invention provides methods of assessing a Pnmt-positive cardiac progenitor cell for its ability to regenerate cardiac tissues in vivo. For example, in such methods, a Pnmt-positive cardiac progenitor cell is obtained and transferred into a subject in need thereof. The fate of the transferred progenitor cell is then monitored in vivo. In certain cases, the transferred progenitor cell contains a marker, such as GFP, luciferase, and beta-galactosidase. To illustrate, the transferred progenitor cell can be monitored (tracked) by magnetic resonance imaging (MRI) or by bioluminescence imaging (BLI).

Development and application of non-invasive imaging techniques to physically and functionally assess the potential of novel cardiac progenitor cells to regenerate damaged myocardium has clear clinical significance. Repair and replacement of damaged cardiac muscle tissue is a key limitation in the prognosis for recovery from ischemic and other forms of heart disease. There is a great need for new approaches to this enduring problem, since heart disease is the leading killer in the United States. New strategies for regenerating damaged cardiac muscle could be readily translated to the clinical setting if first shown to be effective in animal models.

Accordingly, the present invention relates to use of molecular imaging techniques in vivo to evaluate the novel progenitor cell-based strategy for cardiac regenerative medicine. Specifically, this application contemplates methods for detecting and quantifying molecular and cellular pathways that regulate heart function, and methods for cell tracking in vivo for applications in cell-based therapeutics. For example, cardiac progenitor cells of the invention can be transplanted into damaged hearts and these cells can be tracked in vivo using modified magnetic resonance and bioluminescent imaging methods.

One specific embodiment of the invention is a method of identifying and selecting cardiac progenitor cells based on their ability to express knock-in reporter genes from the endogenous Pnmt gene locus. These cells can be isolated in vitro, loaded to magnetic microsphere particle beads, and transplanted into regions of the heart damaged by myocardial infarction. Thus, another embodiment of the invention provides methods of molecular imaging of cardiomyocytes progenitor cells (the method is also referred to as cardiac imaging) to track and study the functional development of these novel progenitor cells in vivo. Optionally, the subject methods of cardiac imaging are performed in small animals.

In certain embodiments, the present invention includes application of non-invasive molecular and cellular imaging techniques that would facilitate development and characterization of progenitor cell strategies in the heart because they permit repeated assessments of the transplanted cells in vivo without the need to sacrifice the animals or subject them to complicated invasive procedures. Several different in vivo imaging approaches have been developed, such as MRI and BLI.

MRI has been used for many years to assess anatomical and physiological parameters in vivo; however, the use of MRI to follow (track) specific cell populations in the cardiovascular system has only recently been described in a few published reports. Of particular interest for Applicant is the discovery that it is possible to "load" cells with magnetic nanoparticles (e.g., ferrodex) in vitro and track these cells with MRI after they have been transplanted into the heart (or other organs/tissues) in vivo. Remarkably, cells loaded with these magnetic particles appear to be relatively stable in vivo, which makes it possible to track transplanted cells over several days, weeks, and perhaps months.

In contrast to MRI, BLI technology is primarily based on the ability to detect light emitted from expression of the firefly luciferase reporter gene in the presence of the substrate, luciferin. Although this technology has been used for many years as a way to quantitate reporter gene activity in transiently transfected cells in vitro, only recently has it been adapted for in vivo imaging applications. Several studies have, for example, demonstrated that luciferase activity can be detected in anesthetized mice using a specialized ccd videocamera set-up in a dark room. To date, most of these studies have fused a strong viral promoter to drive high levels of luciferase activity in target tissues. Certain embodiments of the invention contemplate fusion of strong cell type-specific promoters to luciferase so that the differentiation state of transplanted cells can be assessed by evaluating activation of luciferase expression over time in vivo using BLI.

Methods of Treatments

In certain embodiments, the present invention provides methods of preventing or correcting developmental defects (e.g., cardiac or neuronal), or treating complications (conditions, disorders or diseases) arising later in life. Such methods involve administering to a subject in need thereof the Pnmt-positive progenitor cells of the invention.

In one embodiment, the Pnmt-positive progenitor cells of the invention are useful to replace lost cardiomyocytes or to increase the overall numbers of cardiomyocytes in patients suffering from a myocardiac injury. Myocardial injury refers to damage to the muscle or the "myocardium" in the wall of the heart as a result of disease or trauma. Myocardial injury can be attributed to many things, such as cardiomyopathy, myocardial infarction, or congenital heart disease.

A "cardiomyocyte" is a cell of the cardiac muscle that is striated like skeletal muscle, having microscopically visible myofilaments arranged in parallel with the sarcomere. Cardiac muscle can generate its own excitatory impulses from the sino-atrial node, which acts like a biological pacemaker. In this manner, the contracting signal for cardiac muscles originates in the heart itself. However, the autonomic nervous system can exert control over how fast the signals form and propagate through the heart, which regulates the rate of myocardial contraction.

Cardiomyopathy refers to any disease or dysfunction of the myocardium (heart muscle) in which the heart is abnormally enlarged, thickened and/or stiffened. As a result, the heart muscle's ability to pump blood is usually weakened. The disease or disorder can be, for example, inflammatory, metabolic, toxic, infiltrative, fibroplastic, hematological, genetic, or unknown in origin. There are two general types of cardiomyopathies: ischemic (resulting from a lack of oxygen) and non-ischemic. Ischemic cardiomyopathy is a chronic disorder caused by coronary artery disease—a disease in which there is atherosclerotic narrowing or occlusion of the coronary arteries on the surface of the heart. Coronary artery disease often leads to episodes of cardiac ischemia, in which the heart muscle is not supplied with enough oxygen-rich blood. Eventually, the heart muscle enlarges from the additional work it must do in the absence of sufficient oxygen-rich blood.

Congenital heart disease refers to a condition that is present at birth and often as the heart is forming even before birth. Congenital heart disease may affect the heart, the heart's valves, the veins leading to, or the arteries leading away, from the heart, or the connections between these parts of the body.

Accordingly, in certain embodiments, the present invention provides methods of treating or preventing heart disorders such as cardiomyopathy, myocardial infarction, congenital heart disease, heart failure, and any kind of cardiac dysfunction. Heart failure generally refers to the inability of the heart to supply sufficient oxygenated blood to meet the metabolic needs of the tissues and cells in an individual. This can be accompanied by circulatory congestion, such as congestion in the pulmonary or systemic veins. As used herein, the term heart failure encompasses heart failure from any cause, and is intended herein to encompass terms such as "congestive heart failure," "forward heart failure," "backward heart failure," "high output heart failure," "low output heart failure," and the like. Conditions that could lead to heart failure include, but are not limited to, coronary artery disease, cardiomyopathy, or congenital heart disease.

Cardiac dysfunction is understood to include any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial ischemia and infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). See Braunwald, Heart Disease: a Textbook of Cardiovascular Medicine, 5th edition 1997, W B Saunders Company, Philadelphia Pa. (hereinafter Braunwald).

In another embodiment, the Pnmt-positive progenitor cells of the invention are useful to replace lost neuronal cells or to increase the overall numbers of neuronal cells in individuals in order to treat neurodegenerative disease (disorder or condition) and neurological trauma. Examples of neurodegenerative diseases include, but are not limited to, Huntington's Disease (HD), Alzheimer's Disease (AD), and Parkinson's Disease (PD). The Pnmt-positive progenitor cells can be transplanted into any area from which neural progenitor cells can be obtained that serves to restore function to a degenerated area of the host's nervous system, particularly the host's central nervous system (CNS). To illustrate, suitable areas include the cerebral cortex, cerebellum, midbrain, brainstem, spinal cord and ventricular tissue.

In certain embodiments, the present invention relates to use of Pnmt-positive progenitor cells that are immunologically blinded or immunoprivileged, such that in allogeneic or xenogeneic transplants, they are recognized as self by the recipient, and are not MHC restricted by class I or class II antigens. For example, these cells do not express MHC class I and/or class II antigens. Alternatively, progenitor cells isolated from a non-human mammal according to the invention are transplanted into a human subject. Prior to the transplantation step, the progenitor cells may be cultured, and/or expanded and/or differentiated.

In certain embodiments, the progenitor cells of the invention can be treated by gene therapy to correct a genetic defect and introduced into a patient to restore cardiac or neuronal function.

In one embodiment of the invention, the Pnmt-positive progenitor cells can be differentiated either in culture or in vivo by applying one or more growth factors, or other treatments such as transfection with a nucleic acid molecule, that results in differentiation of the progenitor cells to cardiomyocytes or neuronal cells.

In another embodiment of the invention, the Pnmt-positive progenitor cells can be transplanted without any ex vivo treatment and the appropriate growth factors can be provided in situ within the patient's body. In yet another embodiment, the progenitor cells can be treated with growth factors or other agents ex vivo and subsequently transplanted into the patient in a partially differentiated or terminally differentiated state. Other aspects of the invention include methods of transfecting progenitor cells, dosages and routes of administration, pharmaceutical compositions, donor-isograft protocols, and immunosuppression methods.

The invention specifically contemplates transplanting into patients isogeneic, allogeneic, or xenogeneic progenitor cells, or any combination thereof.

Mode of Administration

In certain embodiments, the present invention provides methods of treating a disease or a tissue injury by delivering the Pnmt-positive progenitor cell to a diseased or injured target tissue (e.g., heart). In certain specific aspects, the present invention provides composition and methods of tissue engineering. Tissue engineering provides the opportunity to generate living substitutes for tissues and organs, which may overcome the drawbacks of classical tissue reconstruction. Optionally, the method can be used alone or in combination with other therapies.

In one embodiment, the present invention provides a tissue engineering composition which comprises: a) a Pnmt-positive progenitor cells; and b) a biocompatible scaffold. Such tissue engineering composition generates a scaffold graft to be delivered to a target tissue.

In certain embodiments, the present invention provides a method of delivering a scaffold graft in a target tissue, comprising: a) seeding the Pnmt-positive progenitor cell onto a scaffold, thereby forming a scaffold graft; and b) implanting the scaffold graft from (b) in direct contact with, or adjacent to, a target tissue for a sufficient time, wherein cells of the target tissue associate with the implanted scaffold graft, thereby to form new tissue. For example, the scaffold graft can be delivered in a heart tissue by surgical implantation. Optionally, such methods may further comprise removing the scaffold graft from the subject. For example, the scaffold graft removed from the subject (i.e., the scaffold and the tissue it bears at the end of the implantation period) can then be re-grafted into another target tissue.

As described herein, the biocompatible scaffold can consist of bioresorbable or non-bioresorbable materials. If the scaffold consists of a single bioresorbably material, it is preferably one that does not significantly resorb during the period of time when the target tissue is being laid down on or within it. Such scaffolds generate a scaffold graft that includes living cells and essentially retain their shape and mechanical integrity. In some instances, it may be preferable to use scaffolds containing bioresorbable materials that lose, for example, less than a 2% of their weight during the same period. If the scaffold is constructed with two or more bioresorbable materials, it may be preferable to select the bioresorbable material that provides the scaffold with its structural integrity according to these criteria.

In certain embodiments, the bioresorbable materials for the biocompatible scaffold include bioresorbable polymers or copolymers that comprise the following monomers or mixtures of polymers and/or copolymers formed thereby: hydroxy acids, particularly lactic acid; glycolic acid; caprolactone; hydroxybutyrate; dioxanone; orthoesters; orthocarbonates; aminocarbonates.

Optionally, the bioresorbable materials can also include natural materials such as collagen, cellulose, fibrin, hyaluronic acid, fibronectin, chitosan, or mixtures of two or more of these materials. The bioresorbable materials may also comprise devitalized xenograft and/or devitalized allograft. Bioresorbable ceramics can also be included within the scaffold. Bioresorbable materials are well known in the art, including, for example, poly(lactic acid), poly(glycolic acid), polydioxanone, polyhydroxybutyrate, and poly(trimethylene carbonate), or mixtures thereof. Poly(lactic acid) has good mechanical strength and does not resorb quickly. Thus, its mechanical properties can be retained for a time sufficient for tissue in-growth to occur (at which point the tissue can assume some, if not all, of the load-bearing function of the scaffold (see A. G. A. Coombes and M. C. Meikle, "Resorbable Synthetic Polymers as Replacements for Bone Graft," Clinical Materials, 17:35-67, 1994).

Non-bioresorbable materials are also well known in the art, including, for example, polyesters, particularly aromatic polyesters, such as polyalkylene terephthalates; polyamides; polyalkenes such as polyethylene and polypropylene; poly (vinyl fluoride), polytetrafluoroethylene carbon fibres; silk (natural or synthetic); carbon fibre; glass; and mixtures of these materials. An advantage of non-bioresorbable materials is that they essentially retain their initial mechanical properties.

In certain embodiments, the biocompatible scaffold can include certain additional components. For example, the scaffold may include bioactive factors, such as growth factors, hormones, catecholamines (norepinephrine or epinephrine), extracellular matrix proteins, cytokines or chemokines.

In other embodiments, hydrogels can also be included in the biocompatible scaffold. For example, the hydrogel can be incorporated within and/or around the scaffold prior to implantation to facilitate the transfer of cells and other biological material (e.g., growth factors) from the surrounding tissue into the scaffold. Hydrogels include positively charged, negatively charged, and neutral hydrogels, and can be either saturated or unsaturated. Examples of hydrogels are TETRONICS™ and POLOXAMINES™, which are poly (oxyethylene)-poly(oxypropylene) block copolymers of ethylene diamine; polysaccharides, chitosan, poly(vinyl amines), poly(vinyl pyridine), poly(vinyl imidazole), polyethylenimine, poly-L-lysine, growth factor binding or cell adhesion molecule binding derivatives, derivatized versions of the above (e.g., polyanions, polycations, peptides, polysaccharides, lipids, nucleic acids or blends, block-copolymers or combinations of the above or copolymers of the corresponding monomers); agarose, methylcellulose, hydroxyproylmethylcellulose, xyloglucan, acetan, carrageenan, xanthangum/locust beangum, gelatine, collagen (particularly Type 1), PLURONICS™, POLOXAMERS™, POLY(N-isopropylacrylmide), and N-isopropylacryhnide copolymers.

EXEMPLIFICATION

The following materials and methods were used in carrying out the work described herein. The invention now being generally described, it will be more readily understood by reference to the following examples, which are included merely for purposes of illustration of certain aspects and embodiments of the present invention, and are not intended to limit the invention.

Example 1

PNMT is a Novel Marker for Cardiomyocyte Progenitor Cells

1. Introduction

Epinephrine (EPI) and norepinephrine (ME) are the major peripheral catecholamines produced in mammals. They are synthesized via the enzymatic conversion of dopamine to NE by the action of dopamine β-hydroxylase (Dbh) and, subsequently, of NE to EPI by the action of phenylethanolamine n-methyltransferase (Pnmt) (Cooper et al., 1991, Norepinephrine and Epinephrine. In The biochemical basis of neuropharmacology, (New York: Oxford University Press), pp. 220-284). In adult mammals, this synthesis occurs primarily in the adrenal medulla and in the sympathetic nervous system. Mice that lack the ability to produce NE and EPI due to targeted disruption of the Dbh gene die in utero from apparent cardiac failure (Thomas et al., 1995, Nature 374, 643-646).

The vast majority of Dbh mouse embryos die before the adrenal gland even forms and before maturation of the sympathetic nervous system, suggesting that the primary source(s) of catecholamine biosynthesis in the embryo must be different from that in adult mice (Thomas et al., 1995, Nature 374, 643-646). One potential source is the heart itself, where Applicant and others have shown that ICA cells are present beginning at relatively early stages (E9.5 in rat; E3 in chick) of cardiac development (Ignarro and Shideman, 1968, J. Pharmacol. Exp. Ther. 159, 38-48; Ebert et al., 1996, J. Mol. Cell. Cardiol. 28, 1653-1658; Huang et al., 1996, J. Clin. Invest 98, 1298-1303; Ebert and Thompson, 2001, Circ. Res 88, 117-124). A specific developmental role for these ICA cells remains elusive, but Applicant has recently shown that they are transiently and progressively associated with regions of the heart that become pacemaking and conduction tissue (Ebert and Thompson, 2001, Circ. Res 88, 117-124). This association was initially observed in the sinoatrial node (SAN) and atrioventricular canal (AVC) regions at approximately embryonic day 11.5 (E11.5) in the rat The clustering of ICA cells in these regions then declined over the next several days of development, but re-appeared along the crest of the ventricular septum (bundle of His region) and, somewhat more sporadically, trailing down the ventricular septum towards the apex at approximately E16.5. These patterns of ICA cell distribution were transient, lasting not more than a 1-2 days in each of these locations. It was not clear if this progressive appearance and disappearance of ICA cells in these various cardiac regions was due to migration, differentiation, and/or death of ICA cells.

To help resolve these possibilities, Applicant has developed a mouse genetic model for studying the fate and function of adrenergic cells in vivo. Specifically, the Cre-recombinase gene was inserted into the endogenous Pnmt locus (Pnmt-Cre) so that Cre-recombinase expression would be directed by Pnmt regulatory DNA sequences. Upon crossing these Pnmt-Cre mice to the reporter R26R strain of mice, Applicant anticipated activation of LacZ expression exclusively in adrenergic cells via Cre-mediated recombination of upstream 1oxp sites flanking a DNA sequence responsible for blocking transcription of the LacZ gene (Soriano, 1999, Nat. Genet. 21, 70-71). In this system, 1acZ expression does not require the continuous activation of Pnmt-Cre. Rather, the genetic changes induced at the Rosa26 locus by transient expression of the Cre-recombinase permanently mark the altered cells and their descendants as β-galactosidase positive and, therefore, provide a means to follow the fate of adrenergic derived cells throughout development In addition, because the targeted insertion of Cre recombinase disrupted the expression of the Pnmt gene, Applicant could assess the potential consequences of selective adrenergic deficiency in these mice. This is the first report to demonstrate that targeted disruption of Pnmt gene expression leads to EPI deficiency, and it is also the only study to show that the fate of adrenergic cells can be effectively mapped in vivo. These efforts have led to the rather surprising and novel finding that adrenergic cells contribute much more extensively to myocardial development than previously appreciated.

2. Results

To determine whether epinephrine plays an important role during development and to identify adrenergic cell descendants in the developing mouse, Applicant inserted the Cre-recombinase gene into the mouse Pnmt locus so the expression of Cre-recombinase would be dependent upon Pnmt regulatory sequences (FIG. 1A). Specifically, Applicant inserted the Cre-recombinase gene into exon 1, creating a gene fusion of the 5' leader sequences from Pnmt directly to Cre-recombinase open reading frame. This strategy was designed to disrupt functional expression of Pnmt while permitting expression of Cre-recombinase exclusively in adrenergic cells. Verification of the correct targeting of the Cre-recombinase insert was confirmed by Southern blotting using 5' and 3' probes each external to the targeting vector (FIG. 1B).

Two of the correctly targeted clones were further propagated and introduced into mouse blastocysts, and independent lines of founder mice were produced. These founder mice were crossed with wild type C57B/6 females to generate F1 animals used in all subsequent studies. Germ-line transmission of the Pnmt-Cre allele was verified initially by Southern blotting and then by PCR (FIG. 1C). When F1 heterozygotes were intercrossed, mice harboring the disrupted Pnmt allele were born in normal Mendelian ratios. 35+/+:75+/−: 46−/− were the actual numbers of mice born as compared with 39, 78, and 39 mice expected for each genotypic class from 156 total progeny (P value=0.410 using the Chi square test). The −/− mice appear overtly normal and are fertile even in −/−×−/− crosses.

The absence of Pnmt expression was predicted to result in mice that cannot produce epinephrine. To test this hypothesis, Applicant measured epinephrine (EPI) and norepinephrine (NE) concentrations in adrenal extracts from $Pnmt^{+/+}$, $Pnmt^{+/Cre}$, and $Pnmt^{Cre/Cre}$ mice by radioimmunoassay (Table 1). EPI was not detectable in extracts from $Pnmt^{Cre/Cre}$ mice, and the concentration of NE was found to be significantly greater in $Pnmt^{Cre/Cre}$ relative to $Pnmt^{+/+}$ and $Pnmt^{+/Cre}$ extracts (P<0.001). In contrast, NE and EPI concentrations were similar in extracts from $Pnmt^{+/+}$ and $Pnmt^{+/Cre}$ mice. These results show that targeted insertion of Cre recombinase effectively disrupted Pnmt expression and production of EPI in homozygous $Pnmt^{Cre/Cre}$ mice, but that heterozygous $Pnmt^{+/Cre}$ mice were indistinguishable from wild-type ($Pnmt^{+/+}$) mice in terms of adrenal NE and EPI content.

Figure 2:
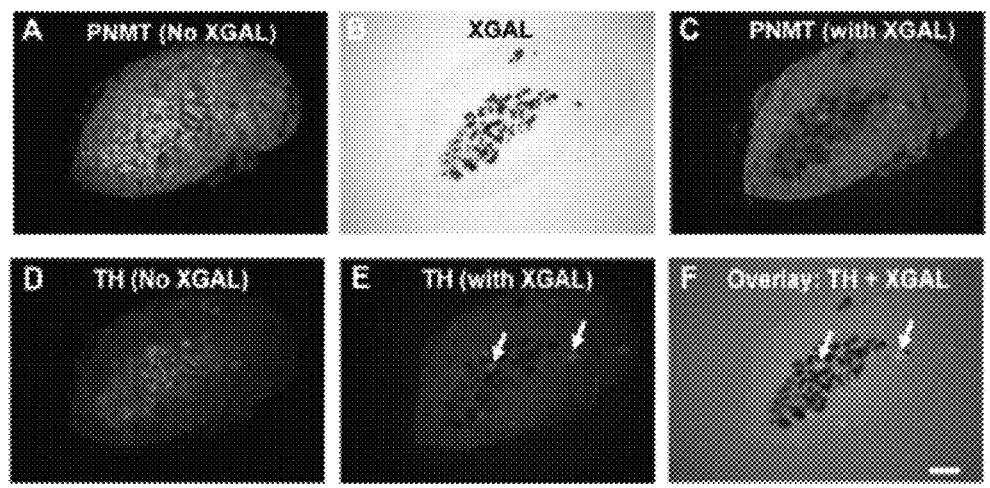
FIGS. 2A-2F show co-immunofluorescent and XGAL histochemical staining in neonatal adrenal sections in Pnmt-Cre/R26R mice. (A) PNMT immunofluorescent histochemical staining (FITC filters). (B) Adjacent section stained with XGAL. (C) PNMT immunofluorescent histochemical staining of the section shown in (B) after XGAL staining. Note that the XGAL staining blocks the fluorescent signal in co-stained cells. (D) TH Immunofluorescent histochemical staining (Texas Red filter) of the same section as shown in (A). (E) TH Immunofluorescent histochemical staining of an adjacent section (same section as shown in panels B&C) after XGAL staining. (F) Overlay of images in panels D and E showing TH Immunofluorescent and XGAL staining simultaneously. Arrows in panels E and F indicate examples of TH$^+$ cells that were not stained with XGAL. Scale bar, 0.1 mm.

TABLE-US-00001 TABLE 1 Adrenal catecholamine content (pg/ng protein). Genotype NE EPI $Pnmt^{+/+}$ (n=5) 14.2.+−.0.6 24.6.+−.2.9 $Pnmt^{+/Cre}$ (n=10) 17.8.+−.1.4 25.0.+−.2.8 $Pnmt^{Cre/Cre}$ (n=4) 32.8.+−.2.6* n.d. n.d. not detected (<0.004 pg/ng) *p<0.001 compared to $Pnmt^{+/+}$ and $Pnmt^{+/Cre}$ To map the developmental distribution of Pnmt-Cre-expressing cells and their descendants, mice heterozygous for the insertion ($Pnmt^{+/Cre}$) were mated with R26R mice, homozygous at the ROSA26 reporter locus. Cells in R26R mice have the ability to robustly express the bacterial LacZ (β-galactosidase) gene if activated by Cre-recombinase (due to removal of a floxed transcriptional block) (Soriano, 1999, Nat. Genet. 21, 70-71). To determine if applicant's system was working, Applicant first examined β-galactosidase staining in adrenal glands where the expression patterns of Pnmt are well-documented and relatively simple. As illustrated in FIG. 2A, Pnmt Immunofluorescent staining is concentrated in the adrenal medulla. An adjacent section stained with XGAL to detect LacZ expression (blue cells) produced a nearly identical pattern of staining (FIG. 2B). When Pnmt immunofluorescent staining was performed on this section after the XGAL staining, little or no fluorescently-stained cells were observed because the XGAL blocked or quenched the fluorescence in co-stained cells (FIG. 2C). Thus the localization of Pnmt and β-galactosidase appear to be completely coincident here. As a control, the same sections were also stained for Th to independently identify chromaffin cells (FIGS. 2D, E, F). Th staining was similar to Pnmt and XGAL staining in these sections, but there were a few cells that stained positively for Th that were not stained with XGAL (FIGS. 2E&F, arrows). These Th+LacZ– cells presumably represent the minority of chromaffin cells that are known to be noradrenergic rather than the adrenergic majority (Coupland and Tomlinson, 1989, Int. J. Dev. Neurosci. 7, 419-43; Ebert and Thompson, 2001, Circ. Res 88, 117-124). Together, these results demonstrate that LacZ expression was highly selective in adrenal sections where it was confined to adrenergic (Pnmt$^+$) cells.

Figure 3:
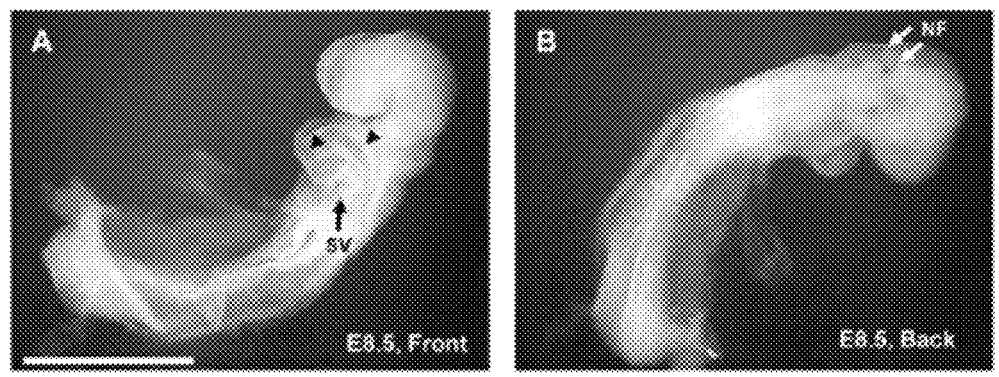
FIGS. 3A-3B show whole-mount XGAL staining of an E8.5 Pnmt-Cre/R26R embryo. (A) Left ventral view. Arrow points to LacZ$^+$ blue-stained cells in the sinus venosus (SV) region. Arrowheads indicate positions of additional LacZ$^+$ cells in this heart. (B) Right dorsal view. Arrows point to LacZ$^+$ blue-stained cells along the dorsal crest of the neural folds (NF). Scale bar, 1.0 mm.

To evaluate Pnmt-Cre expression in the developing mouse embryo, applicant performed whole-mount staining with XGAL. The earliest stage of development when LacZ expression could be detected was embryonic day 8.5 (E8.5). LacZ expression was observed in the heart (FIG. 3A) and along the dorsal ridges of the neural folds in the region of the midbrain-hindbrain junction (FIG. 3B). Within the heart, there appears to be a small cluster of LacZ$^+$ cells in the sinus venosus region (FIG. 3A, arrow), with a few additional LacZ$^+$ cells apparent in the ascending loop and also near the atrioventricular junction (see arrowheads, FIG. 3A).

Figure 4:
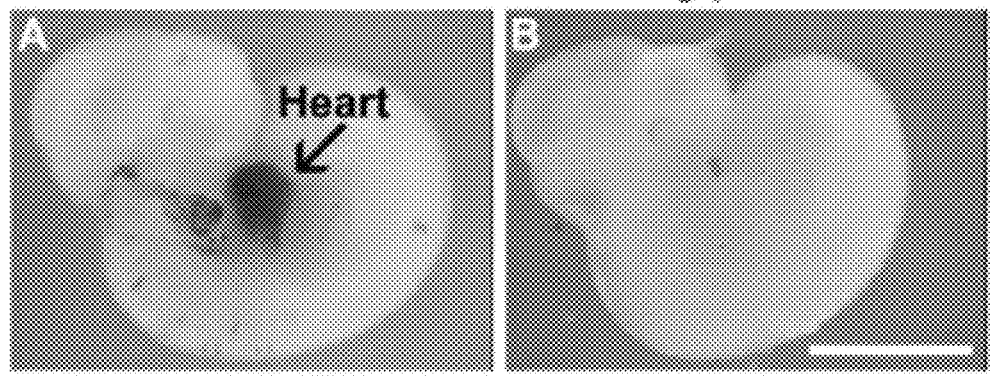
FIGS. 4A-4B show whole-mount XGAL staining in E10.5 mouse embryos. (A) Pnmt-Cre/R26R and (B) Wild-type (Pnmt$^{+/+}$)/R26R mouse embryos at E10.5. Right sagittal views are shown. The arrow depicts the heart. Staining can also be seen in the brainstem and 2nd branchial arch regions. Sparse patches of XGAL staining are also seen along the back (dorsal surface) and in the forelimb of the Pnmt-CrexR26R embryo. Scale bar, 1.0 mm.

Over the next two days, LacZ expression became much more widespread in the heart, as shown in FIG. 4A. By this time, LacZ expression was also evident in the brainstem region, 2nd branchial arch, and sporadically along the dorsal surface of the embryo. LacZ expression was dependent upon Cre-recombinase expression from the Pnmt locus since none was observed when wild-type embryos were similarly crossed with R26R mice (FIG. 4B).

Figure 5:
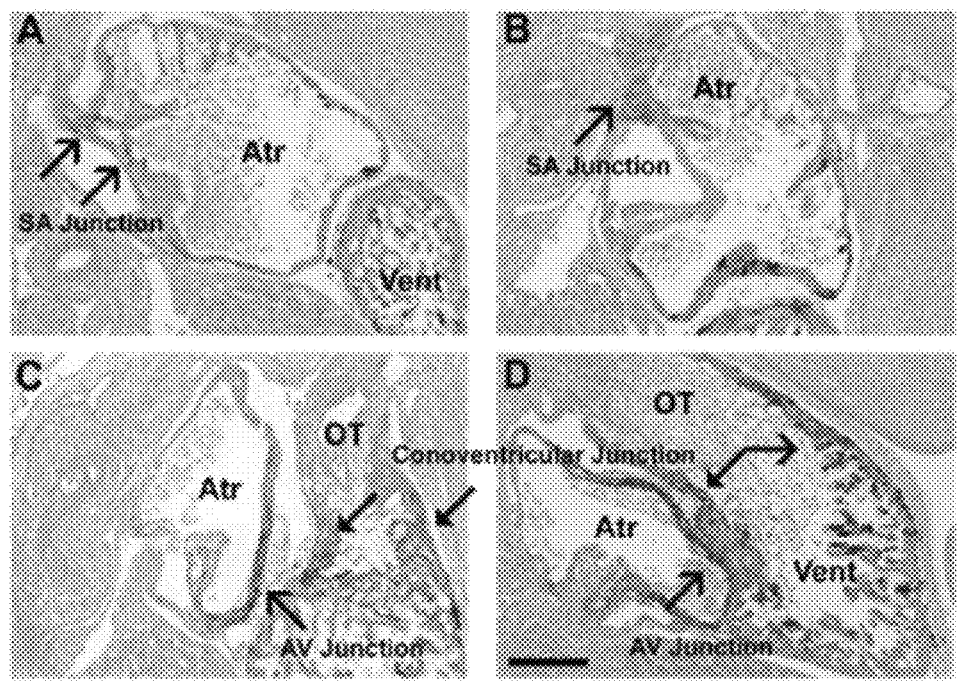
FIGS. 5A-5D show identification of LacZ$^+$ cells in E10.5 mouse heart sections. (A-D) Series of sagittal sections from left to right through an E10.5 heart from a Pnmt-Cre/R26R embryo that was stained with XGAL and counterstained with eosin are shown. Arrows depict areas of the heart that were stained blue with XGAL. Abbreviations: Atr, atrial chamber, AV, antrioventricular; OT, outflow tract SA, sinoatrial; Vent, ventricular chamber. Scale bar, 0.1 mm.

Although it appears from the whole-mount staining (FIG. 4A) that the entire heart was expressing LacZ at this stage of development, examination of heart sections from these embryos revealed that the true staining pattern was more restricted (FIG. 5). Sporadic staining of cardiac cells was observed in the atrial and ventricular regions, including cells in the trabecular region of the ventricle. As shown in FIG. 5, LacZ expression was observed in the SA junction region (FIG. 5A-B); however, the strongest LacZ staining was found near the AV and conoventricular junction regions (FIG. 5C-D). These LacZ expression patterns were consistently observed at this stage of development, and they appear similar to the pattern of catecholamine-producing cells previously reported at a comparable developmental stage in the rat (Ebert and Thompson, 2001, Circ. Res 88, 117-124).

Figure 6:
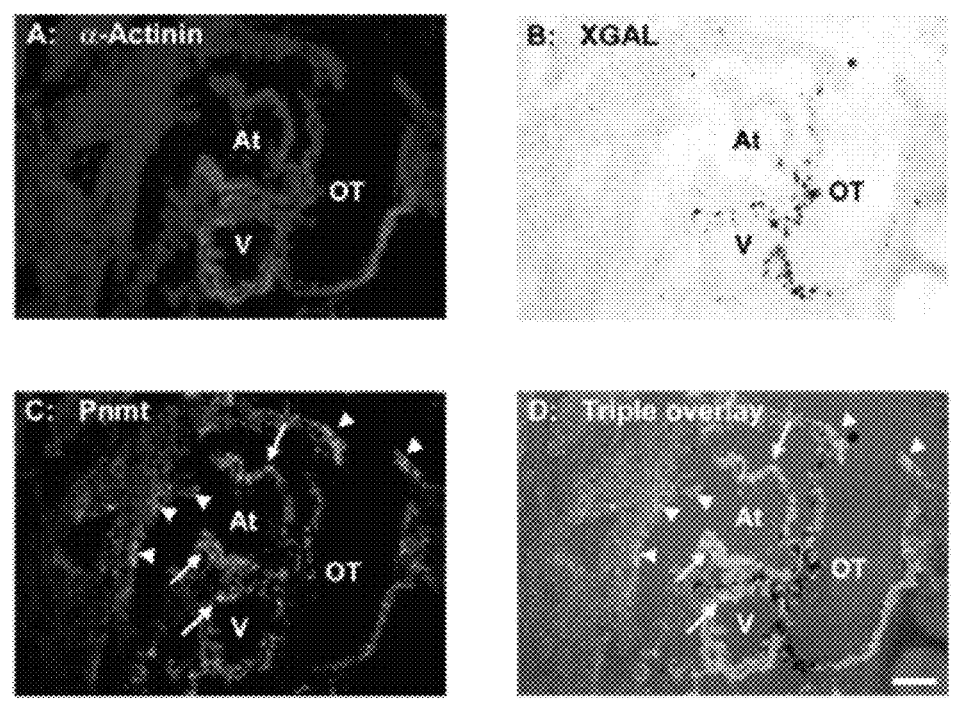
FIGS. 6A-6D show co-immunofluorescent and XGAL histochemical staining in an E9.5 Pnmt-Cre/R26R mouse heart. The same section is shown in panels A-D (right sagittal view). (A) Sarcomeric α-actinin, a myocyte-specific marker, is visualized as Texas Red fluorescent staining. (B) Bright-field image depicting LacZ$^+$ cells (stained blue with XGAL). (C) Pnmt, an ICA cell marker, is seen as green (FITC) fluorescent staining. (D) Overlay image showing all three staining patterns simultaneously. Yellow regions represent apparent co-staining for sarcomeric α-actinin and Pnmt (arrows). The arrowheads depict regions of the embryo that were stained exclusively for Pnmt. Scale bar, 0.1 mm.

The pattern of LacZ expression in the heart appears to be restricted to myocardial cells. To further evaluate this observation, Applicant performed triple-labeling experiments whereby Pnmt-Cre/R26R heart sections (E9.5) were stained for expression of (i) a muscle-specific marker, sarcomeric α-actinin (red fluorescence, FIG. 6A), (ii), LacZ as a marker for cells descended from an adrenergic lineage (blue XGAL staining, FIG. 6B) and (iii) an adrenergic cell marker, Pnmt (green fluorescence, FIG. 6C). Extensive overlap of these three staining patterns could be observed by merging the individual staining panels into a single "overlay" image, as shown in FIG. 6D. The yellow regions represent cells that co-express α-actinin and Pnmt (arrows point to some examples of overlapping expression patterns). Some cells are clearly red or green, but many yellow cells can also been seen in this image. Notably, most of the exclusive green (Pnmt$^+$/α-actinin) cells in the overlay image (FIG. 6D) were found just outside the heart, in both the anterior region adjacent to the outflow tract as well as in the posterior region adjacent to the atrial chamber (indicated by the arrowheads, FIG. 6C-D). The LacZ$^+$ cells (blue) were again found concentrated at junction regions, specifically between the atrial, ventricular, and outflow tract cavities.

By E15.5, the heart has matured morphologically to assume its adult-like appearance. To determine if Pnmt-expressing cells contribute to pacemaker cells in the sinoatrial node (SAN), Applicant performed a preliminary immunofluorescent histochemical staining analysis of wild-type E15.5 mouse embryo sections using an antibody that recognizes the Hyperpolarization-activated cyclic nucleotide-modulated channel isoform 4 (HCN4), a major pacemaker channel protein expressed in the SAN (Garcia-Frigola et al., 2003, Gene Expr. Patterns. 3, 777-783; Stieber et al., 2003, Proc Natl. Acad. Sci. USA 100, 15235-15240). As shown in FIG. 7A, HCN4 staining is highly restricted to the SAN region of the right atrium (arrow), and to a lesser extent, the AVN region (arrowhead). In contrast, sarcomeric α-actinin was found to be expressed throughout the myocardium in this section (FIG. 7B). These data confirm that HCN4 was localized to pacemaker cells in the developing mouse heart.

As shown in the series of sections from a Pnmt-Cre/R26R embryo, LacZ expression not only persists in the heart at E15.5, but is highly pervasive throughout the myocardium in all four chambers (FIG. 7C-E). By far, the strongest and most extensive labeling was found in the ventricular septum, with the most prominent staining appearing at the crest of the septum and extending laterally into both ventricular chambers along the base as well as caudally down the septum towards the apex. LacZ expression in the free walls of both chambers was considerably more sparse than that found in the septum, with a tendency to be localized in cells near the endocardial surface, though LacZ$^+$ cells were also clearly seen in the mid- and epicardial regions of the ventricular myocardium. There appeared to be little or no LacZ expression in the aorta (Ao), aortic valves (AoV), and mitral valves (MiV), all of which can be clearly seen as non-stained tissue in FIG. 7D; however, the myocardial region immediately adjacent to the intake region of each of these valves was strongly labeled with blue XGAL stain.

Figure 7:
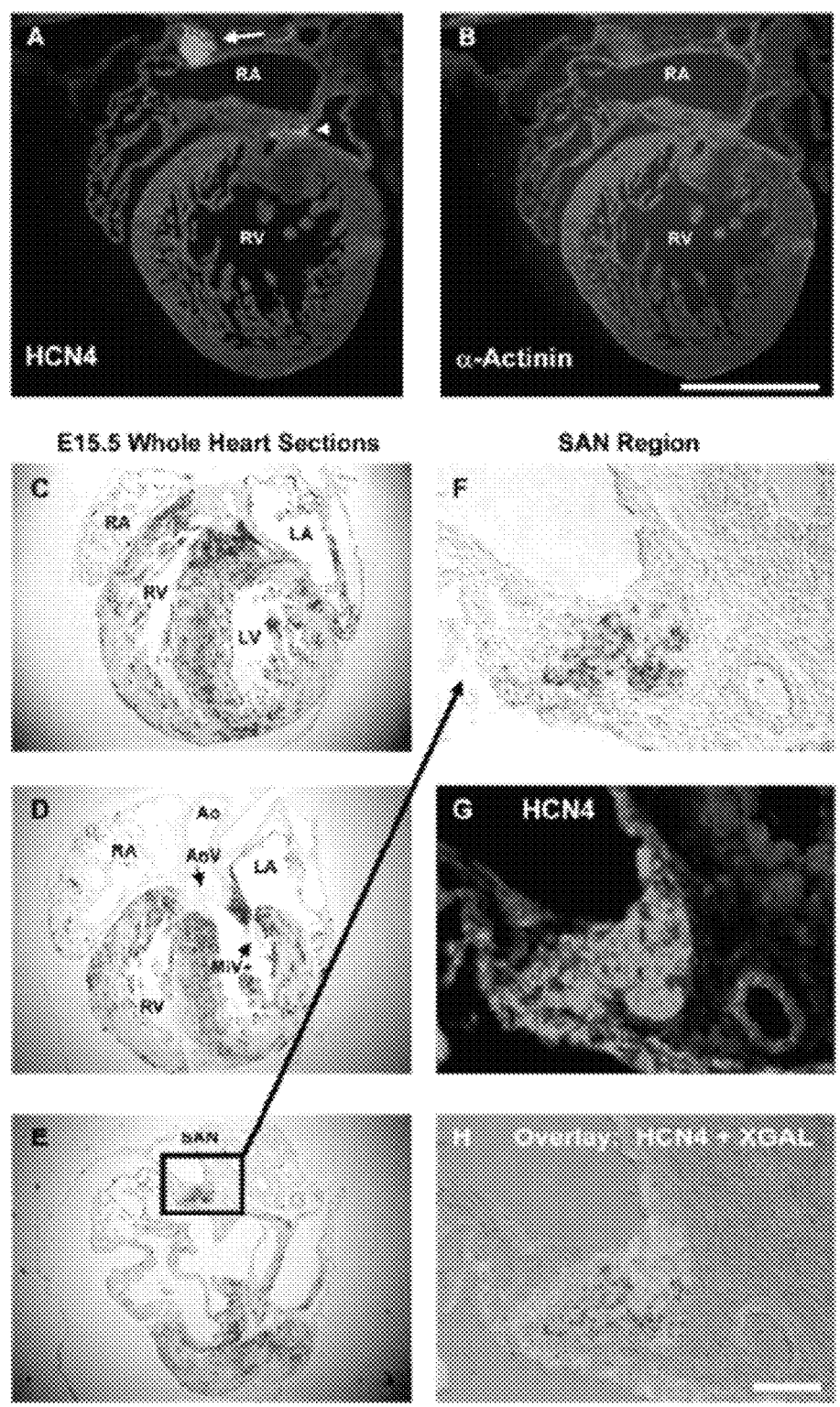
FIGS. 7A-7H show Pnmt-Cre expression in the SAN region of E15.5 mouse hearts. Communofluorescent histochemical staining of wild-type (Pnmt$^{+/+}$) E15.5 mouse heart sections for (A) HCN4 (Arrow depicts SAN myocytes, and arrowhead indicates presumptive AVN myocytes), and (B) Sarcomeric α-actinin. RA, right atrium; RV, right ventricle. Scale bar, 1.0 mm. (C--H) Frontal series of E15.5 Pnmt-Cre/R26R heart sections stained for expression of LacZ (C-E) and the pacemaker channel protein, HCN4 (panels G & H). An expanded view of the boxed region (SAN) in panel E is shown in panel F. Upon switching to dark-field fluorescence microscopy with FITC filters, HCN4 staining can be seen in this section (panel G). To evaluate co-staining for XGAL and HCN4 in this section, the images in panels F and G were combined to produce the Overlay image depicted in panel H. Abbreviations, Ao, aorta, AoV, aortic valve, MiV, mitral valve; SAN, sinoatrial node (boxed region of panels E & F). Scale bar (for panels F--H), 0.1 mm.

Within the atria, LacZ expression was sporadic, with the majority of atrial myocytes appearing as non-stained cells. The exception to this pattern of atrial staining appeared in the sinoatrial node (SAN) region where a strong clustering of blue LacZ$^+$ cells was evident (FIGS. 7 E & F). To show that these cells were SAN myocytes, Applicant performed immunofluorescent histochemical staining of the sections with the anti-HCN4 antibody. As shown in FIGS. 7G & H, HCN4 expression is robust in this region and overlaps extensively with the XGAL staining. These results demonstrate that many, but not all, of the presumptive pacemaker cells (HCN4+) in the SAN also expressed LacZ in these Pnmt-Cre/R26R mice.

Although LacZ expression is found in pacemaker cells as Applicant has just shown, it is clear from the data presented thus far that LacZ expression in the heart extends well beyond the SAN region. By E15.5, most of the LacZ-expressing cells are found throughout the myocardium, as indicated above (see FIG. 7C-E).

Figure 8:
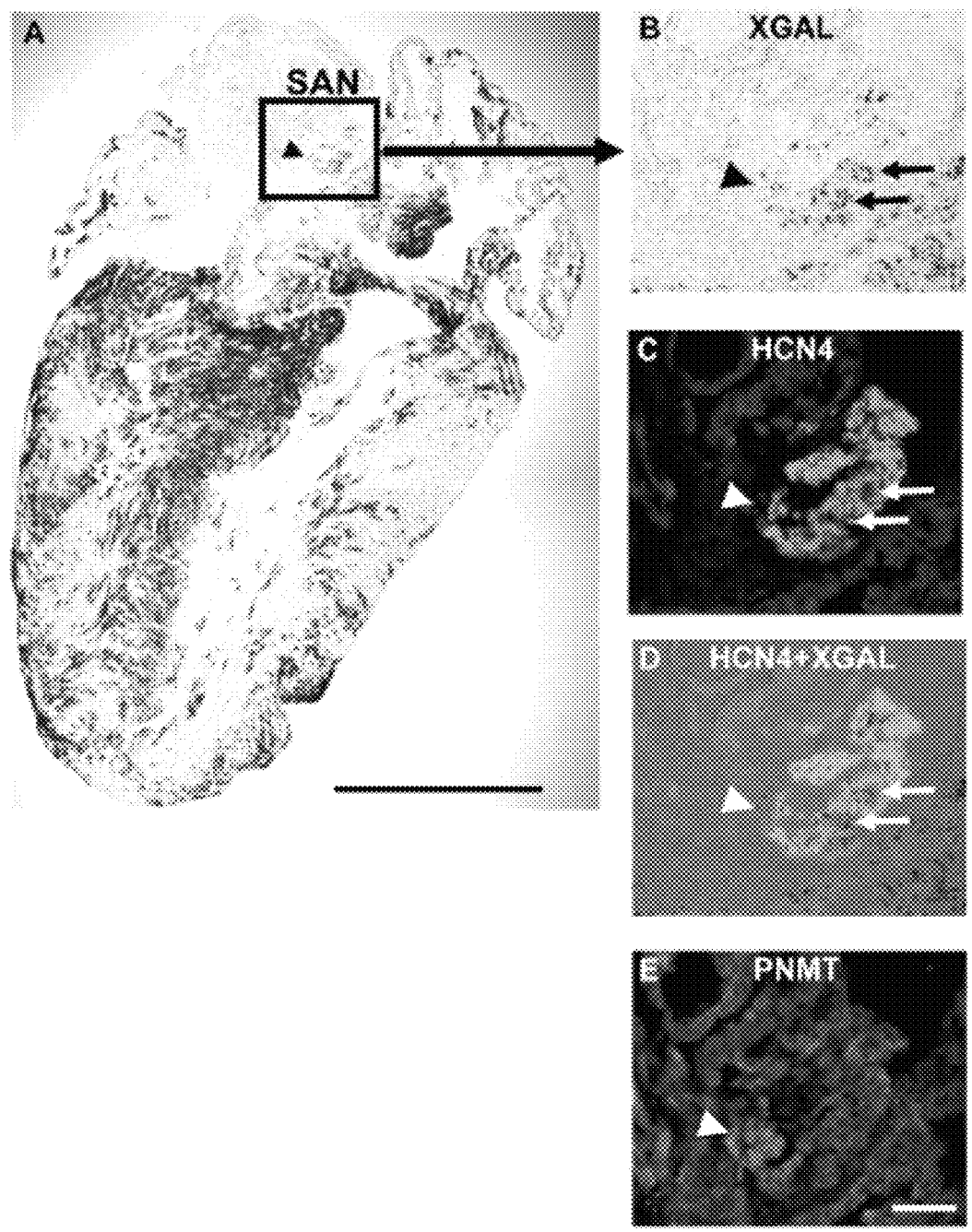
FIGS. 8A-8E show LacZ expression patterns in neonatal mouse heart I: SAN region. (A) Low magnification (4× objective) frontal view of an XGAL-stained Pnmt-Cre/R26R heart section at P2. The SAN region is boxed. Scale bar, 1.0 mm. (B-E) Higher-magnification (20× objective) view of the boxed region from panel A. (B) Bright-field image of blue XGAL-stained cells in the SAN region. (C) HCN4 immunofluorescent (green) staining of the same section shown in panel B. (D) Overlay image of panels B and C. (E) Pnmt immunofluorescent (green) staining of an equivalent region to that shown in panels B-D from an adjacent section. Scale bar, 0.1 mm. Arrowheads point to the equivalent region in each panel where Pnmt$^+$ cells were found. Arrows in panels C and D indicate examples of pacemaker cells co-stained for HCN4 and XGAL.

This pattern of LacZ expression persisted in the heart through at least the early postnatal period. As shown in FIG. 8, extensive XGAL labeling was observed throughout the heart, and was especially dense in the ventricular septum. Many of the pacemaker cells (HCN4$^+$) were also stained blue with XGAL (FIG. 8B-D). Endogenous Pnmt expression in the SAN region was extremely weak at this stage of development (Postnatal day 2, P2), being at best confined to a small cluster of cells (see arrowhead, FIG. 8E).

3. Materials and Methods

A) Creation of Pnmt-Cre Knock-in/Knockout Mice

To construct targeting vector pKP506 Applicant first isolated and subcloned a 7 kb SacI fragment from bacterial artificial chromosome 238M20 (Genome Systems). This fragment carries Pnmt exon 1 and includes 3.3 kb upstream of the ATG initiation codon and also 3.7 kb of sequences 3' of the translation start site. A 1.4 kb SexA1 fragment carrying exon 1 was next subcloned and mutagenized using the Gene Editor Mutagenesis Kit (Promega) to add a unique EcoRI site in place of the normal Pnmt translation initiation codon. A cassette carrying the Cre-recombinase gene fused to a nuclear localization signal (NLS) was then inserted at this unique EcoRI site so that the expected mRNA product is a fusion of the Pnmt 5' untranslated leader to sequences encoding the Cre-recombinase protein. The cassette also included NeoR sequences flanked by FRT recombination sites. This modified SexAI fragment was then exchanged with its wild-type cognate on the SacI clone. Finally the diptheria toxin A gene (DT-A) was added adjacent to the 5' Pnmt flank for negative selection.

Forty-five micrograms of linearized vector DNA were electroporated into R1 mouse embryonic stem cells. G418-resistant clones were isolated and their DNAs characterized by Southern blotting using probes external to the targeting vector (FIG. 1). Cells from two positive clones were injected into C57BL/6 blastocysts and chimeric mice from these injections were mated to C57BL/6 females. Genotypes at the Pnmt locus were identified by PCR analysis using the following primers: Primer 21 (5'-CAGGCGCCTCATCCCTCAG-CAGCC-3', SEQ ID NO: 1); Primer 22 (5'-CTGGC-CAGCGTCGGAGTCAGGGTC-3', SEQ ID NO: 2); and Primer 23 (5'-GGTGTACGGTCAGTAAATTGGACAC-CGTCCTC-3', SEQ ID NO: 3). These amplification reactions yield products of 200 and of 160 bp for the wild-type and the mutant alleles, respectively. Pnmt$^{Cre/+}$ mice were then intercrossed or mated to R26R reporter mice as described in the text.

B) Catecholamine Radioimmuno-Assays

Epinephrine and norepinephrine concentrations were measured by radioimmunoassay as described previously (Ebert and Thompson, 2001, supra). Briefly, adrenal glands were isolated from decapitated neonates and immediately frozen on dry ice. Individual adrenal gland extracts were prepared by sonication for 10 sec in 0.1 M HCl, followed by microcentrifugation (14,000×g, 10 min) to remove residual debris. The extracts were assayed using a commercially available radioimmunoassay (ALPCO Labs, Inc., Wyndham, N.H.), and protein concentrations were determined using the Bio-Rad (Hercules, Calif.) protein assay. Equivalent amounts of protein (5 ng/sample) were assayed in a volume of 0.25 mls. Results are expressed as Mean.+−.S.E.M. and compared for statistically significant differences by one-way analysis of variance (ANOVA) with p<0.05 required to reject the null hypothesis.

C) Whole-Mount Staining for β-Galactosidase Activity

Embryos were staged by timed matings. Females carrying a vaginal plug were removed from the mating cage and noon of that day was considered to be E0.5. Isolated embryos were fixed 50 minutes at 4.degree. C. in PBS containing 2% paraformaldehyde (w/v) and 2% glutaraldehyde (v/v). Embryos were rinsed at 4.degree. C. with PBS three times for 30 minutes each and then incubated in PBS containing 1 mg/ml XGAL (5-bromo-4-chloro-3-indoyl-beta-Dpyranoside), 5 mM ferricyanide, 5 mM ferrocyanide, 2 mM $MgCl_2$, and 0.2% Ipegal CA-630 (Sigma). After 15 hours at 30.degree. C., the embryos were rinsed in PBS containing 3% DMSO and then stored at 4.degree. C. in PBS.

D) Immunofluorescent Histochemical Staining

Co-immunofluorescent histochemical staining was performed essentially as described previously (Ebert and Thompson, 2001, supra). Primary antibodies used in this study include rabbit polyclonal antibodies from Chemicon International (Temecula, Calif.) that selectively recognize either Pnmt (AB110) or HCN4 (AB5808), and mouse monoclonal antibodies from Sigma-Aldrich (St. Louis, Mo.) that selectively recognize either Th (T1299) or sarcomeric α-actinin (A7811). Fluorescently-tagged secondary antibodies were obtained from Jackson Immunolabs (Denver, Pa.), and include fluorescein isothiocyanate (FITC)-conjugated donkey anti-rabbit IgG and Texas Red-conjugated donkey anti-mouse IgG. All antibodies were used at 1:100 dilution, except for the anti-HCN4 antibody, which was used at 1:50 dilution.

Embryos were isolated from timed-pregnant females and fixed with freshly prepared 4% paraformaldehyde in 0.1 M phosphate buffered saline, pH 7.3 for 1-2 hours on ice. The samples were then transferred to 30% sucrose solution in PBS, pH 7.3, and allowed to equilibrate at 4.degree. C. for at least 48 hours. The sucrose-saturated samples were then shipped to FD Neurotechnologies, Inc. (Catonsville, Md.) for sectioning (20 μm) and mounting onto SuperFrost Plus microscope slides (Fisher Scientific, Inc., Pittsburgh, Pa.). The sections were then frozen and stored at −80.degree. C. for subsequent use.

To perform the immunostaining procedure, the slides were first thawed at room temperature, and each section was ringed with a PAP pen (Research Products International, Mount Prospect, Ill.) to form an incubation well. The tissues were then rehydrated with PBS for 20 minutes, followed by incubation with blocking solution (0.3% Triton X-100, 5% powdered nonfat dry milk, and 0.02% sodium azide in PBS) for 20-30 minutes at room temperature. The blocking solution was then replaced with fresh blocking solution containing the primary antibody (for co-staining, two different primary antibodies were included in the same incubation solution). Primary antibody incubations proceeded for one hour at room temperature and then overnight at 4.degree. C. in a humidified chamber. Following this incubation period, the primary antibody solutions were removed and the sections washed three times (10 minutes each) in PBS at room temperature. All remaining steps were performed at room temperature. Fluorescently-tagged secondary antibodies were incubated with the sections for 2 hours at room temperature in the dark. The secondary antibody solutions were then discarded and the sections washed in three successive changes of PBS. Slides/coverslips were mounted with VectaShield mounting medium (Vector Laboratories, Burlingame, Calif.).

For experiments where XGAL staining and immunofluorescent labeling were combined, Applicant first performed the XGAL staining on the sections overnight as described above. The XGAL solution was then removed, and the sections were washed with PBS (3×10-mins each) prior to initiating the immunofluorescent staining as described in the preceding paragraph. Digital images were collected using a Nikon Eclipse E1000 fluorescence microscope, and processed for display using Adobe Photoshop 5.5 software.

Example 2

Roles of Catecholamines in Cardiac Development

The goal of this Example is to understand how catecholamines influence heart development. Genetic studies have shown that catecholamines are essential for proper embryonic development because mice lacking the ability to produce noradrenaline (norepinephrine) and adrenaline (epinephrine) die from apparent cardiovascular failure in utero (Thomas et al., 1995, supra). The specific function of catecholamines in cardiac development, however, has not been elucidated. Applicant's research has shown that the heart itself is a source of epinephrine production at early stages of development (Ebert et al., 1996, supra), and that epinephrine-producing cells are transiently clustered in pacemaking and conduction centers (SA node, AV node, His bundle, ventricular septum) (Ebert and Thompson, 2001, supra). These findings have prompted applicant to propose that catecholamines are essential for cardiovascular development because they stimulate pacemaking activity and facilitate the differentiation of conduction tissue. Three specific aims are described as follows:

Specific aim 1 is to identify and characterize adrenergic cells in the embryonic mouse heart. This aim is to test the hypothesis that catecholamine-producing cells are pacemaker cells in the embryonic mouse heart. The following experiments are carried out.

One experiment is to perform co-immunofluorescent staining for adrenergic and pacemaker markers. The objective is to determine if catecholamine biosynthetic enzymes (i.e., PNMT, DBH, and TH) are expressed in pacemaker cells in the embryonic mouse heart. The rationale is that, if adrenergic cells are pacemaker cells, then Applicant should expect to find them in pacemaker regions of the developing mouse heart, as Applicant has seen in the embryonic rat heart. Further, pacemaking proteins (e.g., HCN1&4 channel proteins) and catecholamine biosynthetic enzymes (PNMT, DBH, and TH) would be expected to be co-expressed in the same cells.

Applicant utilizes dual immunofluorescent histochemical staining techniques to study the temporal and spatial expression patterns of catecholamine biosynthetic enzymes and pacemaker proteins in the developing mouse heart. The staining is performed essentially as described in Example 1. Embryos are isolated from timed-pregnant wild-type mice at E7.5, E8.5, E9.5, E10.5, E12.5, E14.5, and E18.5, and processed for immunofluorescent histochemical staining. An outline of the co-staining strategy is depicted in Table 2.

TABLE-US-00002 TABLE 2 Co-immunofluorescent histochemical staining strategy outline. Primary antibody pairs Secondary antibodies Rabbit anti-PNMT+Mouse anti-TH+ FITC-conjugated Donkey Mouse anti-α-actinin*anti-rabbit IgG+Texas Red-conjugated Donkey anti-mouse IgG Rabbit anti-DBH+Mouse anti-TH+Same as above Mouse anti-α-actinin*Rabbit anti-HCN4+Mouse anti-TH+Same as above Mouse anti-α-actinin* Rabbit anti-HCN1+Mouse anti-TH+ Same as above Mouse anti-α-actinin* *Adjacent serial sections are co-stained for the myocyte marker, α-actinin, and the indicated rabbit antibody.

Figure 9:
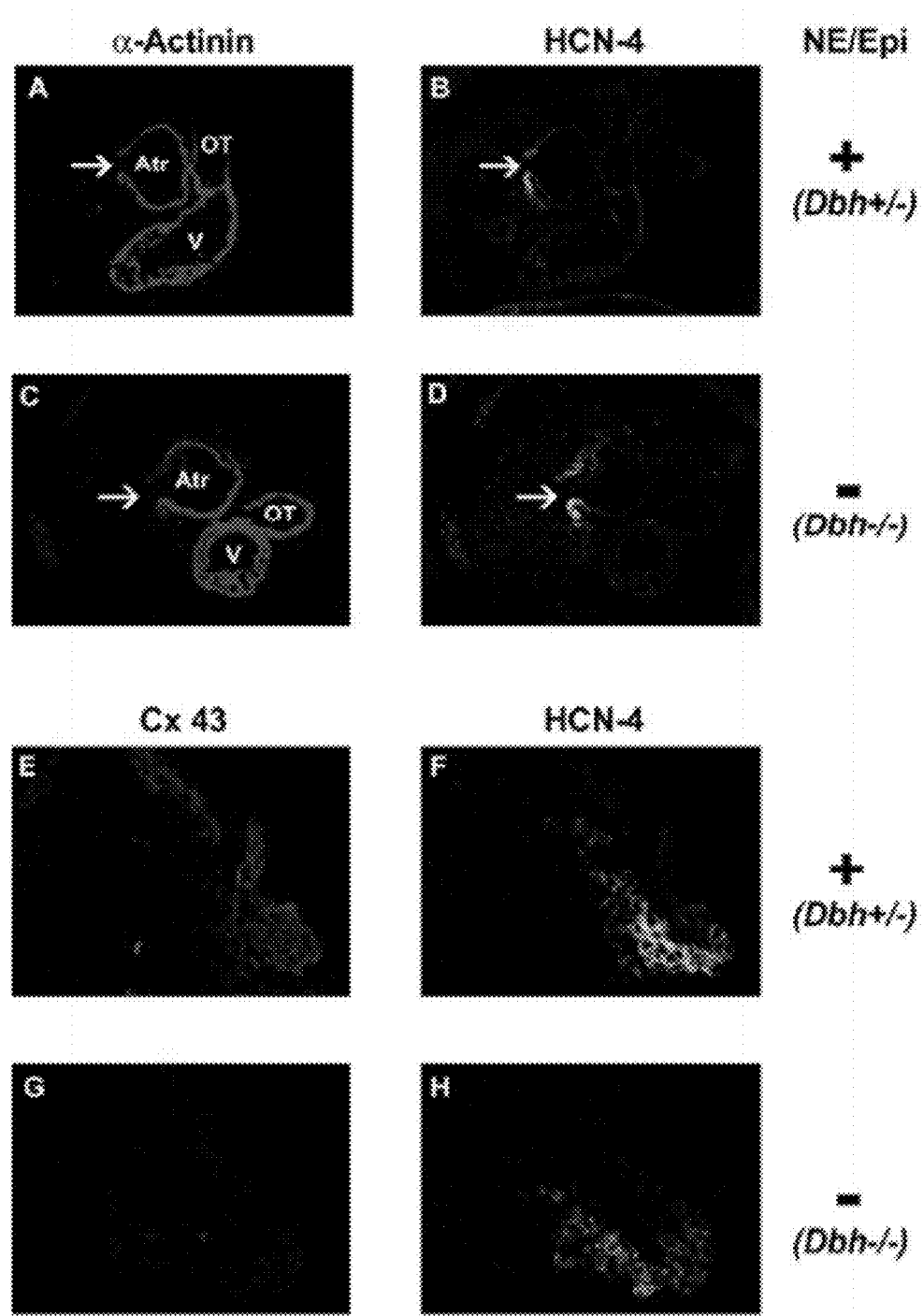
FIGS. 9A-9H show co-immunofluorescent histochemical staining in sagittal sections from E10.5 Dbh$^{+/-}$ and Dbh$^{-/-}$ mouse embryos. (A-D) Low-magnification (10× objective) view of α-actinin and HCN-4 staining in Dbh$^{+/-}$ (A&B) and Dbh$^{-/-}$ (C&D) embryos. The arrow indicates the presumptive SA-node region at the mouth of the inlet to the atrial chamber. (E-H) High-magnification (60× objective) of the SA-node region in an adjacent section co-stained for Cx43 (E&G) and HCN-4 (F&H) in Dbh$^{+/-}$ (E&F) and Dbh$^{-/-}$ (G&H) mouse embryos.

As shown in FIG. 9, the anti-HCN4 antibody selectively identifies presumptive SA nodal cells in the embryonic mouse heart. The specificity of the anticatecholamine biosynthetic enzyme antibodies (TH, DBH, and PNMT) has already been described (see Ebert & Thompson, 2001, supra). In addition, the use of an antisarcomeric α-actinin antibody as a marker for working myocardial cells is well-established. Thus, using these selective marker antibodies, Applicant determines if catecholamine biosynthetic enzymes are expressed in SA nodal cells. Applicant also tests a new anti-HCN1 antibody (from Chemicon International, Inc., Temecula, Calif.) in this assay to determine if it can serve as a useful marker for this experiment. HCN1 is known to be expressed in the developing heart (Shi et al., 1999, Circ Res 85:e1-e6), presumably in pacemaker cells (Mangoni et al., 2001, Cardiovasc Res 52:51-64). The existing markers likely provide informative results regarding coexpression of catecholamine biosynthetic enzymes and pacemaker proteins.

Another experiment is to evaluate Pnmt-GFP knock-in expression in the developing mouse heart. The objective is to determine if expression of GFP faithfully reproduces the pattern of the endogenous Pnmt gene. The rationale is that GFP expression should recapitulate PNMT expression since Applicant has inserted the GFP reporter gene into the mouse Pnmt locus. Applicant expects to find GFP-expressing cells in the embryonic mouse heart clustered around pacemaking and conduction centers. It is likely that GFP expression in these mice aids to identify, isolate, and characterize living cardiac adrenergic cells as described above.

To obtain embryos that are heterozygous for the Pnmt-GFP allele, homozygous Pnmt-GFP males are mated with wild-type females. The embryos are isolated at various embryonic stages, fixed, processed, and sectioned for immunohistochemical staining experiments. Initially, Applicant examines them for expression of GFP using laser-scanning confocal fluorescence microscopy. If GFP expression patterns are reflective of those that Applicant has observed for endogenous PNMT in the developing heart, then Applicant initiates co-staining experiments to help verify that GFP expression is confined to Pnmt-expressing cells. To accomplish this, Applicant uses a rabbit anti-PNMT primary antibody with a Texas Red-conjugated anti-rabbit secondary antibody. Thus, this strategy should allow Applicant to visualize PNMT in the red spectrum and GFP in the green spectrum. Applicant can then overlay the images obtained from each wavelength separately to evaluate the degree of overlapping expression.

Another experiment is to isolate and carry out electrophysiological characterization of cardiac adrenergic cells. The objective of this experiment is to characterize the electrophysiological properties of cardiac adrenergic cells. The rationale is that, if adrenergic cells are also pacemaker cells, then Applicant should expect to find spontaneous action potential generation similar to that observed in SA-nodal cells. In addition, pacemaker currents should be expressed in these cells, while inward rectifiers (e.g., $I_{Kl}$) are not expected to be found in these cells (Mangoni et al., 2001, supra).

Cells are isolated from Pnmt-GFP embryonic mouse hearts, and seeded onto collagen-coated glass coverslips for analyses using whole-cell patch-clamp recording techniques. Applicant patches the fluorescent cells from the mixed population of GFP+ and GFP− heart cells seeded onto the coverslips. Applicant utilizes established protocols to measure action potentials, pacemaker (IF) and other cardiac ion currents ($I_{Ca}$, L, $I_{Ca}$, T, $I_{Na}$, etc.). If GFP-expressing cells are difficult to find, applicant can selectively enrich for them using fluorescence-activating cell-sorting (FACS) strategies. Alternatively, applicant uses the Pnmt-Cre/LacZ mice. In general, the Pnmt-Cre/LacZ mice can serve as a back-up model for essentially all of the experiments that Applicant is proposing with the Pnmt-GFP mice. It is possible, for example, to isolate living LacZ+ cells by pre-incubating them with a fluorescent substrate, fluorescein d1-β-galactoside (FDG) and then using FACS to isolate the LacZ+ cells (Fiering et al., 1991, Cytometry 12:291-301).

Another experiment is to perform gene expression profile(s) of cardiac adrenergic cells. The objective is to identify genes uniquely expressed in cardiac adrenergic cells. The rationale is that Applicant's hypothesis predicts that cardiac adrenergic cells become pacemaker/conduction system myocytes. Applicant expects to find gene expression signatures for pacemaker (HCN) and other cardiac ion channel proteins (e.g., subunits of channels responsible for gating $I_f$, $I_{Na}$, $I_{Ca}$, L, $I_{Ca}$, T, and $I_{Kr}$—all of which have recently been shown to be present in mouse SA nodal cells) (Mangoni et al., 2001, supra). The results of this experiment can identify genes that are uniquely or preferentially expressed in ICA cells, potentially providing novel information about how these cells develop and function.

GFP+ cells are isolated from E10.5 Pnmt-GFP knock-in mouse hearts by enzymatic/mechanical dissociation of embryonic hearts into single cells (Maltsev et al., 1994, Circ. Res. 75:233-244) that are separated into GFP+ and GFP– cell populations using FACS. RNAs are purified from the isolated cells and analyzed using Affymetrix mouse expression chips. Expression patterns for cardiac adrenergic cells (GFP+) are compared to non-adrenergic cardiac cells (GFP–).

Figure 10:
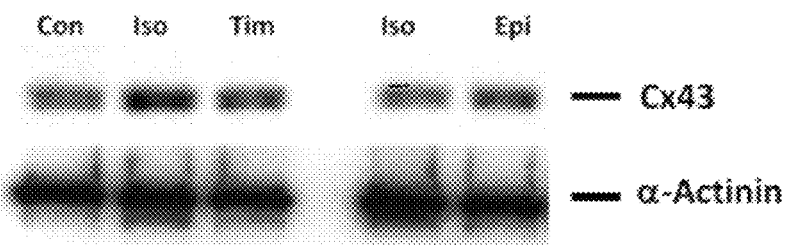
FIG. 10 shows β-adrenergic stimulation of Cx43 expression in cultured neonatal rat cardiomyocytes. The cultures were allowed to develop spontaneous, synchronous beating activity for 7 days prior to drug treatment. The indicated drugs (10 μM each) were added to the culture media from a 100× stock, and the cells were returned to the incubator for 5 hrs. Protein extracts were prepared, separated by SDS-PAGE, electro-transferred to PVDF membrane and reacted with either an anti-Cx43 or an anti-α-actinin antibody. The blots were developed using chemiluminescence and autoradiography. Abbreviations: Con, control (no drugs); Iso, isoproterenol; Tim, timolol; Epi, epinephrine; Cx43, connexin 43.

Applicant has recently performed a pilot gene chip screen using RNA isolated from neonatal rat cardiomyocytes that had been cultured for 10 days in the absence and presence of adrenergic receptor blockers (timolol and phenoxybenzamine, 10 µM each). The samples were analyzed using the Affymetrix Rat Genome U34A GeneChip®, containing 8799 gene fragments that represent all full-length or annotated genes. Interestingly, connexin 43 expression was decreased by ~65% following adrenergic receptor blockade. Cx43 is mentioned only because Applicant has other corroborating data indicating that its expression may be positively influenced by the presence of catecholamines (FIGS. 9-10). Any interesting leads are pursued by first replicating the experimental results, and then using independent, conventional assays such as Northern and Western blots, to confirm (or refute) the gene-chip data (for selected genes).

Specific aim 2 is to map the fate of cardiac adrenergic cells in the developing mouse heart. This aim is to test the hypothesis that catecholamine-producing cells are the progenitors of cardiac pacemaking and conduction system myocytes in the mouse. The following experiments are carried out.

One experiment is to localize Pnmt-Cre/LacZ expression in developing mouse heart. The objective is to identify and map the fate of adrenergic cells in the developing mouse heart. The rationale is that, if adrenergic cells contribute to the development of the pacemaking/conduction system of the heart, then Applicant might expect to find them preferentially localized to regions of the heart that give rise to the SA-node, AV-node, Bundle of His, and Purkinje fibers.

Applicant crosses Pnmt-Cre mice with R26R mice to create embryos that express LacZ only in Pnmt-expressing cells. For early embryonic stages (E7.5-E12.5), whole-mount β-galactosidase staining is performed. Positive staining is intensely blue. Staining patterns are documented using digital photomicroscopy. The stained embryos are then be sectioned, counterstained with eosin, and re-photographed at low and high magnification. Because of diffusion concerns in the larger later stage embryos (E13 and later), whole-mount staining is not performed with them. Instead, isolated embryos or tissues (e.g., heart, adrenal glands) are first fixed and sectioned prior to staining for β-galactosidase. Staining patterns are compared with published histological and anatomical evaluations of mouse cardiac development.

It is clear that LacZ expression in Pnmt-Cre/R26R embryos is not restricted exclusively to pacemaking and conduction centers. The proximal components of the pacemaking/conduction system—i.e., SA node, AV node, and bundle of His regions appear to be included in the β-gal staining results obtained with these mice, but Applicant has not seen any evidence for LacZ localization in Purkinje fibers. If an association with the proximal pacemaking/conduction centers is maintained in the mice, then LacZ expression in Pnmt-Cre/R26R mice could represent a molecular marker that may be used to distinguish between proximal and distal components of the pacemaking/conduction system in the developing heart. Alternatively, Applicant may find that adrenergic cells and their descendents (Pnmt-Cre/LacZ+) are simply in the vicinity of developing pacemaking/conduction centers at certain stages of development, but that they are not actually the pacemaking/conduction myocytes themselves. This issue should be clarified by successfully completing the following co-immunofluorescent staining experiment.

Another experiment is to perform co-immunofluorescent histological staining to identify specific cell types. The objective is to identify the specific cardiac cell type(s) that produce catecholamines in the developing heart. The rationale is that if applicant's hypothesis is correct, then developing SA nodal cells should be LacZ+ in embryos from Pnmt-CrexR26R matings. Applicant's preliminary data suggest that ICA cells are found in pacemaking/conduction system tissue as well as in other parts of the heart. The results from the proposed experiments should provide cell type-specific identification of cells that are ICA descendents. This information is potentially important because it is likely to provide novel insight about fundamental aspects of cardiac development and function.

Applicant performs dual immunofluorescent histochemical staining for β-gal and various cell type-specific markers. Applicant first verifies that β-gal expression occurs in ICA cells by co-staining embryonic sections with anti-β-gal and anti-catecholamine biosynthetic enzyme antibodies. To identify specific cell types, Applicant proposes to use the antibodies listed in Table 3 below.

TABLE-US-00003 TABLE 3 A list of cell type specific antibodies. Cell Type Target Antigens Antibody Source Intrinsic Cardiac PNMT Rabbit anti-PNMT Ebert Adrenergic (ICA) cells TH Mouse anti-TH Sigma ICA+Descendents βgal Mouse anti-βgal Sigma ICA+Descendents βgal Rabbit anti-βgal Chemicon or Hoechst Cardiomyocyte Sarcomeric α-actinin Mouse anti-α-actinin Sigma Pacemaker cells HCN4 pacemaker Rabbit anti-HCN4 Chemicon channel Conduction cells* Connexins (Cx43, Mouse anti-Cx43 Sigma Cx40, and Cx45) Rabbit anti-Cx40 & Cx45 Thompson Neural crest cells AP-2transcript. factor Rabbit anti-AP-2 Santa Cruz Biotech Proepicardial and α4-Integrin Mouse anti-α4 integrin Chemicon neural Rabbit anti-α4 integrin crest cells Endothelial cells PECAM Rat anti-PECAM Pharmingen Smooth muscle cells α-sm. muscle actin Mouse anti-αSMA Sigma *Conduction cells are actually a heterogeneouos collection of cells that express various gap junction proteins (connexins). Each connexin is expressed in a specific non-uniform pattern in the developing heart. Cx43 is most widespread, while Cx40 becomes largely restricted to atrial tissue, and Cx45 is most prevalent in pacemaking and conduction nodes.

Another experiment is to examine proliferative activity of cardiac adrenergic cells. The objective is to determine if cardiac adrenergic cells proliferate in the developing mouse heart. The rationale is that terminally differentiated cardiomyocytes are thought to be largely post-mitotic. Applicant anticipates that cardiac adrenergic cells may represent a transient cardiac phenotype, and they ultimately differentiate into pacemaking and conduction system myocytes. As such, Applicant finds that unlike mature cardiomyocytes, cardiac adrenergic cells still retain proliferative capabilities.

Applicant uses the bromodeoxyuridine (BrdU) labeling strategy for labeling DNA-synthesizing cells in the developing heart (see, e.g., Cheng et al., 1999, Development 126: 5041-5049). Each animal will receive two IP injections of bromodeoxyuridine (160 mg BrdU/kilogram body weight) two hours apart, followed by euthanasia and sacrifice four hours after initial injection, for a total labeling period of 4 hours. Hearts will be immediately removed, flushed with heparinized saline for retrograde aortic perfusion, and fixed by perfusion with methanol/DMSO (80/20). Formaldehyde fixation, as needed for other antibody staining, will require retrieval of BrdU antigenicity with 2N HCl, now routine. Alternatively, if two or three channel immunofluorescence of other markers would be useful, DNA-replicating cells may be labeled with $^3$H-5-methyl-thymidine (IP) for autoradiographic colocalization with fluorescent markers (see, e.g., Sedmera et al., 2002, Anat Rec 267:137-145).

Another experiment is to examine migration capability of cardiac adrenergic cells. The objective is to determine if cardiac adrenergic cells migrate. The rationale is that data from the immunofluorescent and β-gal staining experiments indicate that cardiac adrenergic cells may arise from proepicardium and neural crest, two highly migratory cell types (see e.g., Li et al., 2002, Development 129:2031-2042; Maschhoff and Baldwin, 2000, Am J Med Genet. 97:280-288). Migration of cardiac adrenergic cells is likely to be detected.

Proepicardial and branchial arch regions of the Pnmt-GFP embryos are isolated at E9.5-E10.5 and explanted onto collagen-coated coverslips, cultured and assayed as described by Li et al., 2002, supra). Fluorescent (e.g., GFP-expressing) cells are recorded using fluorescence-based time-lapse video microscopy. Similar assays are performed with enzymatically-dissociated cells isolated from Pnmt-GFP mouse hearts between E8.5 and E11.5. In both assays, Applicant calculates the distance traveled and speed of migration. Fluorescent beads are included in the cultures to provide fixed reference points.

Specific aim 3 is to evaluate the development of pacemaking/conduction tissue function in the absence and presence of norepinephrine and epinephrine. This aim is to test the hypothesis that norepinephrine and/or epinephrine are required for functional development of the cardiac pacemaking/conduction system. The following experiments are carried out.

One experiment is to examine pacemaker/conduction marker expression.+−.catecholamines. The objective is to determine if the expression of pacemaker (HCN4) and conduction (Cx43) system markers is altered in the absence of endogenous catecholamines ($Dbh^{-/-}$ mice) relative to their expression in catecholamine-competent ($Dbh^{+/+}$ or $Dbh^{+/-}$) embryos. The rationale is that, if NE and/or EPI are necessary for pacemaker/conduction system development, then Applicant expects to find altered expression patterns for HCN4, Cx43, and/or additional pacemaker/conduction system markers in catecholamine-deficient hearts.

Applicant compares the expression patterns of HCN4 and Cx43 in catecholamine-deficient ($Dbh^{-/-}$) and normal embryos ($Dbh^{+/-}$) obtained from parental crosses of $Dbh^{+/-}$ male×$Dbh^{-/-}$ female (to preclude rescue of embryonic lethality by maternal sources of NE/EPI). Development of heterozygous ($Dbh^{+/-}$) embryos appears completely normal with no associated embryonic lethality. Thus, Applicant compares HCN4 and Cx43 expression in $Dbh^{-/-}$ and $Dbh^{+/-}$ embryos from the same litters between E8.5 and E10.5, the developmental period immediately preceding the onset of lethality in $Dbh^{-/-}$ embryos. This strategy can be expanded to include other markers as they become available and as warranted by results from the earlier experiments and/or relevant reports published by other groups.

The Dbh knockout mouse model originally described by Thomas et al. (1995, supra) are used for this experiment. Although $Dbh^{-/-}$ embryos die of cardiovascular failure in utero, they can be rescued by administration of DOPS in the maternal drinking water (note that DOPS can be converted to NE in vivo by an alternative pathway). After birth, DOPS is no longer needed for survival or reproduction, so it is completely feasible to generate $Dbh^{-/-}$ dams for this experiment (see FIG. 9). The Dbh gene, not the Pnmt or Th genes, is the key knockout target for this experiment. As describe above, homozygous disruption of Pnmt resulted in loss of EPI production in the developing mouse, but this did not result in any observed lethality or overt phenotype. Thus, EPI is not essential for cardiovascular development (provided that NE is present). On the other hand, loss of EPI and NE is an embryonic lethal phenotype, with $Dbh^{-/-}$ mice dying between E10.5 and E13.5 (Thomas et al., 1995, supra).

Applicant already has $Dbh^{-/-}$ mice and is establishing a small breeding colony of these animals for use in this and subsequent experiments. One alternative strategy would be to selectively eliminate NE/EPI production from cardiac cells using a cardiac-specific Cre-recombinase gene that is expressed at early stages of cardiac development in adrenergic cells.

Another experiment is to evaluate pacemaker activity.+−.catecholamines. The objective is to determine if intrinsic pacemaking activity is altered by the absence of endogenous catecholamines, beating rates are measured from wild-type and catecholamine deficient embryonic hearts under physiologic conditions. Receptor-specific adrenergic drugs are employed to help identify the subtype(s) of adrenergic receptors involved in mediating these responses. The rationale is that, if endogenous catecholamines stimulate pacemaking activity, then Applicant should find that $Dbh^{-/-}$ embryos have slower heart rates than their wild-type siblings. This has already been demonstrated to some extent, though the measurements were performed at room temperature rather than at 37.degree. C. Applicant plans to extend these initial findings by carefully comparing rates at 37.degree. C. in the absence and presence of various adrenergic drugs. NE/EPI or β-agonists should rescue/recover rates. Alpha-adrenergic drugs may also show some activity. Conversely, beating rates in wild-type embryos may be sensitive to adrenergic receptor blockade. Catecholamines can act acutely on pacemaker cells since their absence ($Dbh^{-/-}$ mice) did not appear to alter pacemaker channel expression. Hence, the cellular pacemaker "machinery" appears to be in place, but it still may need some external stimulation by NE/EPI to operate efficiently (e.g., to sufficiently maintain cardiac output at early pre-innervation stages of development).

Applicant sets up matings between $Dbh^{-/-}$ females and $Dbh^{+/-}$ males to generate offspring that are ~50% $Dbh^{-/-}$ (embryonic lethal between E10.5-E13.5) and ~50% $Dbh^{+/-}$ (indistinguishable from wildtype). The embryos are isolated at E10.5 and placed in pre warmed, oxygenated, serum-free culture media (DMEM) for assessment of beating rates in an incubation chamber equipped with an inverted phase-contrast microscope with an attached video camera. The embryos are equilibrated in the culture media under physiological conditions for at least 20-30 mins prior to performing beating rate assessments. Photodiode sensors positioned on the video screen detect light changes that occur as result of cardiac contractions, and these signals are converted to electrical signals that are acquired and analyzed using National Instruments' data acquisition hardware and software (customized LabView 4.0 software). Beating rates are recorded from one embryo at time, and Applicant first obtains a baseline rate before evaluating drug effects. The baseline rate is recorded over 5-10 mins. prior to the addition of indicated drug, as outlined in Table 4 below. The drugs are evaluated over a broad range of concentrations (e.g., 0, 0.01, 0.1, and 1 µM) by progressively increasing the amounts of drug administered to each sample.

TABLE-US-00004 TABLE 4 Outline of drug-testing strategy for beating rate assessments. Drug Receptor Specificity Genotype to be tested Epinephrine Nonselective agonist $Dbh^{-/-}$ Norepinephrine Semi-selective agonist $Dbh^{/-}$ (poor $\beta_2$ agonist Isoproterenol Nonselective $\beta$ agonist $Dbh^{/-}$ Terbutaline Selective $\beta_2$ agonist $Dbh^{-/-}$ Phenylephrine Selective $\alpha_1$ agonist $Dbh^{-/-}$ Timolol Nonselective $\beta$ Wild-type and antagonist heterozygotes ($Dbh^{+/-}$) Atenolol Selection $\beta_1$ antagonist Wild-type and heterozygotes ($Dbh^{+/-}$) Phenoxybenzamine Nonselective $\alpha$ Wild-type and antagonist heterozygotes ($Dbh^{+/-}$) Prazosin Selective $\alpha_1$ antagonist Wild-type and heterozygotes ($Dbh^{+/-}$)

Another experiment is to identify regional action potential (AP) characteristics (conventional microelectrode). The objective is to determine if the absence of endogenous catecholamines alters the generation and/or propagation of electrical signaling in the heart. The rationale is that different regions of the developing heart have characteristic types of action potentials associated with them. If endogenous catecholamines are required to stimulate and help to coordinate electrical signaling activity in the developing heart, then altered action potential profiles in catecholamine-deficient embryos can be detected.

Figure 11:
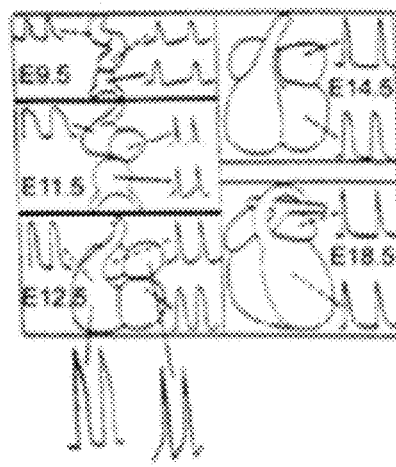
FIG. 11 shows comparison of action potentials recorded from various regions of embryonic rat hearts at different stages of prenatal development. Action potentials that were recorded in my laboratory are shown outside the boxed region of the E12.5 heart diagram.

$Dbh^{-/-}$ and $Dbh^{+/-}$ embryos are isolated at E10.5, decapitated, and placed in a pre-warmed, oxygenated incubation chamber. Using conventional microelectrode recording techniques, Applicant records transmembrane voltages from three regions—atrial, ventricular, and outflow tract. Applicant compares the upstroke velocity, duration, and shape of the action potentials recorded from these specific cardiac regions. As an initial test of the feasibility of this approach, Applicant isolated E12.5 rat embryos and recorded action potentials from different regions of the heart, as shown in FIG. 11. These results, represented by the action potential traces drawn outside the boxed regions in FIG. 11, are similar to those published previously (shown inside the boxes with corresponding heart diagrams for each age).

Another experiment is to perform optical mapping of action potentials using photodiode array detection. The objective is to measure conduction velocity in the absence and presence of endogenous catecholamines. The rationale is that rapid and directed propagation of electrical signals through the myocardium is critical for the development and maintenance of cardiac performance. If catecholamines are required to stimulate the development of the conduction system, then Applicant might expect to find significantly slower conduction velocities and altered vector directions in catecholamine-deficient embryos.

Figure 12:
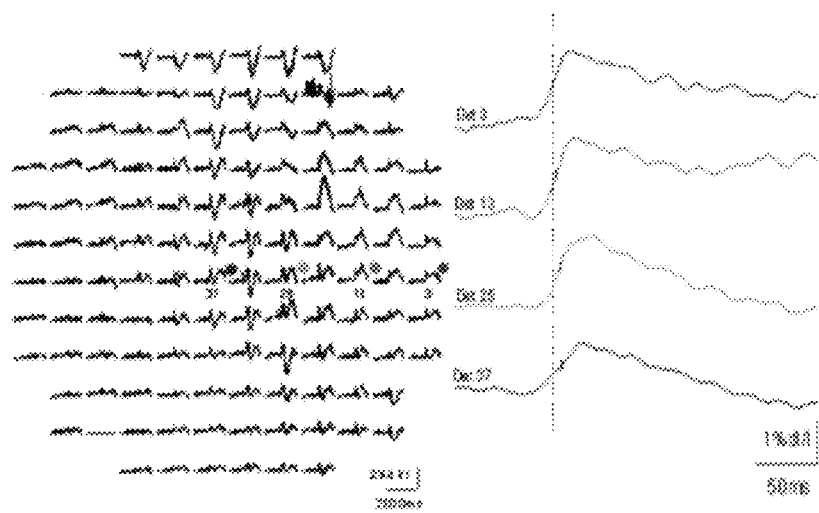
FIG. 12 shows an example of optical mapping experiment using E10.5 mouse heart. Microarray detection of action potentials generated from a spontaneous impulse are shown on the left, and an expanded view of selected action potentials is shown to the right. Time of activation was estimated by comparing the half-maximal intensity signal for each action potential.

To evaluate propagation of the conduction signal through the developing heart, Applicant uses voltage-sensitive dyes and optical (photodiode arrays) imaging techniques to simultaneously record action potentials from many locations and map the direction of conduction in the heart as has been elegantly described in Rentschler et al., 2001, Development 128:1785-1792; Rentschler et al., 2002, Proc Natl Acad Sci USA 99:10464-10469). Applicant has performed some preliminary tests of this experimental strategy using E10.5 mouse hearts in short-term (1-5 hrs) culture. The hearts were stained with di4-ANEPPs, a fluorescent voltage-sensitive dye, and both spontaneous and stimulated electrical activity were recorded using a photodiode array (FIG. 12). In this initial experiment, Applicant estimated the conduction velocity to be ~0.16 mm/msec. The data showed that the signal-to-noise ratio is very large (>10), indicating that the technique is capable of measuring the propagating velocity on a small spatial scale (~20 µm).

Another experiment is to carry out cap junction assays.+-.catecholamines. The objective is to determine if gap junction development is impaired in embryonic hearts from catecholamine-deficient mice. The rationale is that Applicant's preliminary studies suggest that gap junction (Cx43) expression is impaired in $Dbh^{-/-}$ embryos. Gap junction deficiency could compromise the ability of the developing heart to effectively transmit electrical signals through the myocardium, resulting in poor conduction and coordination of electrical activity in the heart. There is also some pharmacological evidence suggesting that gap junction activity can be regulated through adrenergic signaling pathways (for review, see Dhein, 1998). If Applicant can show that gap junction activity is significantly decreased in $Dbh^{-/-}$ embryonic hearts relative to $Dbh^{+/-}$ or $Dbh^{+/+}$ hearts, then such a result would strongly support the data showing that Cx43 expression is reduced in embryos deprived of NE/EPI.

Applicant uses a variation of the fluorescent dye-coupling assays described by Li et al. (2002, supra) and Ai et al. (2000, J Clin Invest 105:161-171) to evaluate gap junction function. Cardiomyocytes are isolated from $Dbh^{-/-}$ and $Dbh^{+/-}$ mouse embryos at E9.5-E10.5, cultured at various densities for 24 hours on collagen-coated glass coverslips, and subjected to the dye-coupling assay. This involves loading fluorescent dye intracellularly via a patch pipette and subsequently counting the number of coupled cells obtained as a result of this treatment (defined as those that become obviously fluorescent after dye injection).

Another experiment is to perform gene expression profiling using gene chip microarray analysis. The objective is to determine if genes encoding for gap junction and other conduction cell proteins are influenced by catecholamines. The rationale is that, if catecholamines influence differentiation of conduction tissue, then Applicant may expect to see altered patterns of conduction system markers in catecholamine-deficient hearts. RNAs are isolated from $Dbh^{-/-}$ and $Dbh^{+/-}$ sibling hearts at E10.5, and used for microarray analysis. This strategy can evaluate how the absence vs. the presence of endogenous catecholamines affects gene expression in the heart. The expression of specific genes as well as patterns of gene expression (cluster analysis) can be evaluated essentially as described above.

Specific Methods

Double immunofluorescent histochemical staining and whole-mount β-galactosidase staining is performed as described above in Example 1.

Isolation of embryonic cardiac cells is performed as described by Maltsev et al. (1999). Briefly, embryonic hearts are isolated by surgical dissection and pooled in Hank's Balanced Salt Solution ($Ca^{++}/Mg^{++}$-free) on ice. The tissue is then be pre-warmed to 37.degree. C., and transferred to pre-warmed collagenase buffer containing 1 mg/ml collagenase B (Roche) and the following (in mM): NaCl (120), KCl (5.4), $MgSO_4 \cdot 7H_2O$ (5), Pyruvic acid (5), Taurin (20), Hepes (10), Glucose (20), and $CaCl_2$ (0.03), pH 6.9. Digestion proceed at 37.degree. C. with intermittent swirling for 30 mins. Collagenase digestion is terminated by the addition of KB buffer consisting of (in mM): KCl (85), $K_2HPO_4$ (30), $MgSO_4 \cdot 7H_2O$ (5), EDTA (1), $Mg_2$ ATP (5), Pyruvic acid (5), Creatine (5), Taurin (20), and Glucose (20), pH 7.2. The tissue is mechanically dissociated by subjecting it to mild rocking for 30 mins. Final dissociation is achieved with mild trituration. Single cells are collected by passing the material through sterile 70 μm mesh filters to remove clumps and other debris. The cells can then either be seed onto collagen-coated coverslips for whole-cell patch-clamp analysis, or then can be further separated into fluorescent and non-fluorescent cardiac cells using FACS.

Action Potential Recordings can be performed as below:

1) Conventional Microelectrodes

Conventional microelectrodes having tip resistance in the range of 15-25 megaohms are pulled on a horizontal micropipette puller (Model P-87, Sutter Instruments Co., Novato, Calif.) from TW120F glass (WPI, Sarasota, Fla.) and filled with 3 M KCl. Microelectrodes are coupled to an electrometer (model 750, WPI, Sarasota, Fla.) whose output is connected to a conditioning amplifier (Meca, Indianapolis, Ind.) that allows both amplification and electronic derivation of voltage with respect to time. The dual voltage outputs of this recording amplifier are connected to an oscilloscope with dual sweep capability (Tektronix, model 5B12N) and an IBM-AT compatible Pentium II computer with a fast A/D board and analysis software (APES, Hugo Sachs Elektronik, March-Hugsgetten, Germany). Applicant's analyses include measurement of the resting membrane potential, upstroke velocity, amplitude, and duration (APD50 and APD90) of the action potentials recorded from analogous regions of wild-type and Pnmt knockout embryonic mouse hearts.

2) Optical Measurements with Voltage-Sensitive Dyes and Photodiode Array Detection Imaging with voltage-sensitive dye (VSD) provides sub-millisecond temporal resolution for examining the synchronization among heart tissue or cultured heart cells. In cultured cells, the sensitivity of the method permits resolution of single action potentials from individual neurons. Thus, the diversity in conductance and the shape of the action potential in the cell population can also be examined. Staining: Heart tissue slice or cultured dissociated cells are incubated for 30 to 60 min in ringer solution containing 0.05 mg/ml of the voltage-sensitive dye Di4-ANEPPS (Molecular Probes, Eugene, Oreg.). The ringer is gently stirred and bubbled with carboxygen and kept at 27-32.degree. C. During this staining period, some dye molecules diffuse to the cell membrane and bind to the lipid bilayer. This dye does not penetrate into the cell. Although the staining is not selective to the cardiac muscle cells, only excitable membrane can generate signal (color change) and dye stained on the connective tissue only contributes to the background fluorescence. The stained preparation is perfused with a warm (34-37.degree. C.), oxygenized Ringer on the stage of an upright microscope. The image of the cells is projected onto a photodiode array, and the dye molecules binding to the membrane convert the transmembrane potential change into the changes in fluorescence intensity. The photocurrent produced by the fluorescent light thus is linearly correlated to the trans-membrane potential of the cells. Optical imaging is performed with a 124-element photodiode array (Centronics Inc., Newbury Park, Calif.) at a frame rate of 1,000 frames/second. A 5× (NA. 0.12, Zeiss) objective is used to project the image of the preparation onto the array where each photodetector receives light from a 0.33×0.33 mm$^2$ area of the slice. The photocurrent of dye-related fluorescent signals (at wavelength of 650 nm) from each photodetector are individually amplified through a two stage amplifier system. The amplifiers perform a current to voltage conversion using a feedback resistor of 1 G-ohm, and then a voltage gain of 1000, and a high-pass filter with a time-constant of 1 sec (0.16 Hz corner frequency). The photocurrent from the photodiode is about 100 pA. The optical signal size (dF/F) was about $1\times10^{-2}$ to $5\times10^{-3}$ of the resting fluorescent intensity. Optical recording trials are usually 20 seconds long, and 30-50 trials are recorded to limit the total exposure time to less than 100 seconds for each preparation. Signals from the photodiode array and two local field potential electrodes are digitized with a 12-bit data acquisition board (Microstar Laboratories, Bellevue, Wash.) installed in a PC. Before digitization, a 4-pole Bessel analog low-pass filter with a 333 Hz corner frequency is applied to all optical channels to ensure that the frequency of the analog signals was lower than the Nyquest frequency of the sampling. Digitized data is directly transferred to the hard disk of the computer for subsequent analysis.

Whole cell voltage-clamp recording—Voltage-clamp studies are performed essentially as described in the preprint article by Katchman et al. (JPET, 2002). The specific protocols for individual current evaluations are provided below:

1) $I_{K1}$-inwardly rectifying background K+ current—The inward-rectifier potassium current ($I_{K1}$) is elicited by command pulses (500 msec duration) from a holding potential −40 mV (to inactivate sodium channels) to between −100 mV and +40 mV at increments of 10 mV. The interval between pulses are 10 seconds.

2) $I_K$-delayed rectifier K$^+$ currents ($I_{Ks}$ and $I_{Kr}$)—The following protocol is used to evaluate the slow component of the delayed-rectifier potassium current ($I_{Ks}$). A 7.5 sec test pulse is delivered from a holding potential of −40 mV to +40 mV in 10 mV increments in the presence of the selective $I_{Kr}$ blocker, E4031 (1 μM), and tail currents are measured upon repolarization to −40 mV. The rapid component of the delayed rectifier, $I_{Kr}$, is measured as the E4031-sensitive difference current using the same protocol except that the duration of the pulse is 1.5 seconds rather than 7.5 seconds. In both cases, the interval between pulses is 20 seconds. The I-V relationships for $I_K$ are constructed by measuring tail currents as previously described (Liu et al., 1998, J Pharmacol Exp Ther 285:672-679; Liu et al., 1998, J Pharmacol Exp Ther 287:877-883).

3) $I_f$-hyperpolarization-activated (pacemaker) current—To evaluate $I_f$, Applicant uses a modification of the protocol described by DiFrancesco et al. (J Physiol 1986, 377:61-88). Briefly, the holding membrane potential is clamped at −40 mV, and long (up to 1.5 seconds) hyperpolarizing pulses in increments of 10 mV are applied from holding potential level up to −130 mV. Applicant considers $I_f$ to be present in a given cell if Applicant observed a cesium-sensitive, time-dependent inward current. These observations are confirmed by blocking the current with the $I_f$-specific inhibitor, ZD7288. I-V relationship is obtained by plotting tail current amplitude versus the tail step potential. The steps (−70 to +10 mV, in increments of 10 mV) are applied following the hyperpolarizing step to −120 mV to maximally activate $I_f$. Reversal potentials and current densities are evaluated as described above.

4) $I_{Na}$-fast inward sodium current—The voltage dependence of activation of $I_{Na}$ is examined using −110 to −90 mV holding potentials. Test pulse of 25 msec duration is applied in increments of 10 mV from −100 to +80 mV. The steady-state inactivation (availability) curves are constructed using a 25 msec test pulse to −30 mV preceded by conditioning pulses from −120 to +20 mV (in 10 mV increments), and (Na$^+$) are symmetrically set at 5 mM. In these experiments high TEA internal and external solutions are used. Calcium currents are blocked by using either nifedipine (1 μM) or 100-200 μM Cd$^{2+}$, and low concentrations (200 μM) of Ca$^{2+}$.

5) $I_{Ca}$,L-L-type calcium Ca$^{2+}$ current—The L-type calcium current is measured as described previously (Liu et al., 1998, J Pharmacol Exp Ther 287:877-883) by holding the membrane potential at −60 to −40 mV to inactivate the sodium current. In addition, TTX (10 μM) is used in some experiments where more negative voltages are required as holding potentials. To examine the voltage-dependence and kinetics of $I_{Ca}$,L, 100-200 ms test pulses from −60 to +80 mV in 10 mV increments are applied. The kinetics of inactivation of this channel are analyzed quantitatively when either $Ca^{2+}$ or $Ba^{2+}$ are the charge carriers through the channel to determine both the $Ca^{2+}$-induced and voltage-mediated components of the inactivation process. The voltage-dependence of steady-state inactivation (availability curves) is constructed using 500 ms conditioning pulses between −100 to +80 mV (given in 10 mV increments from a holding potential of −60 mV) followed by a 100 ms test pulse to 0 mV. Recovery from inactivation and its voltage-dependence is also examined by varying the recovery interval between the test and conditioning pulses at different holding potentials. All solutions have high concentrations of $Cs^+$ and TEA, but contain no $Na^+$. $I_{Ca}$,L is studied both in the basal state (i.e., no added cAMP) and in the fully phosphorylated state (200 μM cAMP) of the channel.

Example 3

Molecular Imaging of Novel Cardiomyocyte Stem Cells

Figure 13:
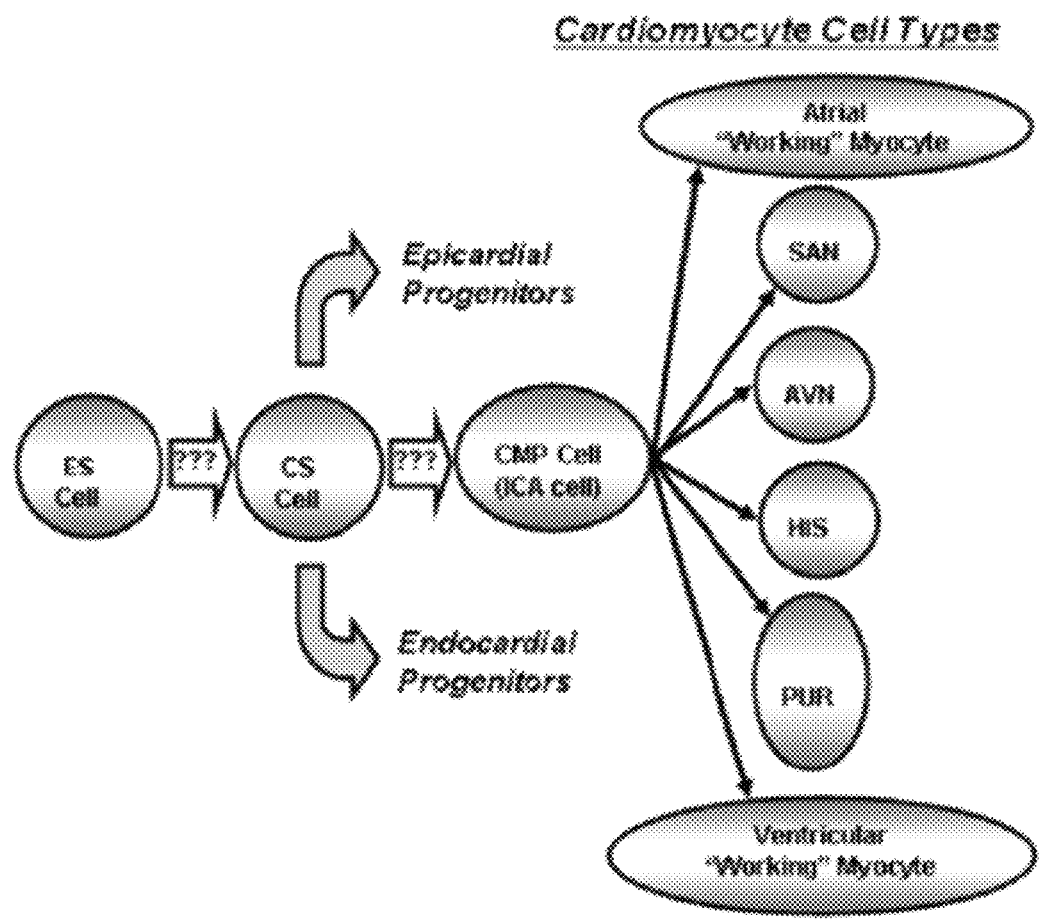
FIG. 13 is a schematic illustration of cardiomyocyte differentiation. This picture represents an overly simplified view of how cardiomyocytes may differentiate from embryonic stem (ES) cells. Alternatively, "ES cells" could be replaced with "fertilized oocyte". The question marks in the block arrows indicate uncertainty about the number of steps required in between the specified cell types shown. Abbreviations, CS, cardiac stem; CMS, cardiomyocyte stem; SAN, sinoatrial node; AVN, atrioventricular node; His, H bundle; Pur, Purkinje fiber.

The goal of this Example is to test the hypothesis that molecular and cellular imaging techniques identify, track, and functionally assess a novel population of cardiomyocyte stem cells for their potential to regenerate cardiac muscle tissue in vivo. A schematic illustration of cardiomyocyte differentiation is shown in FIG. 13.

Figure 14:
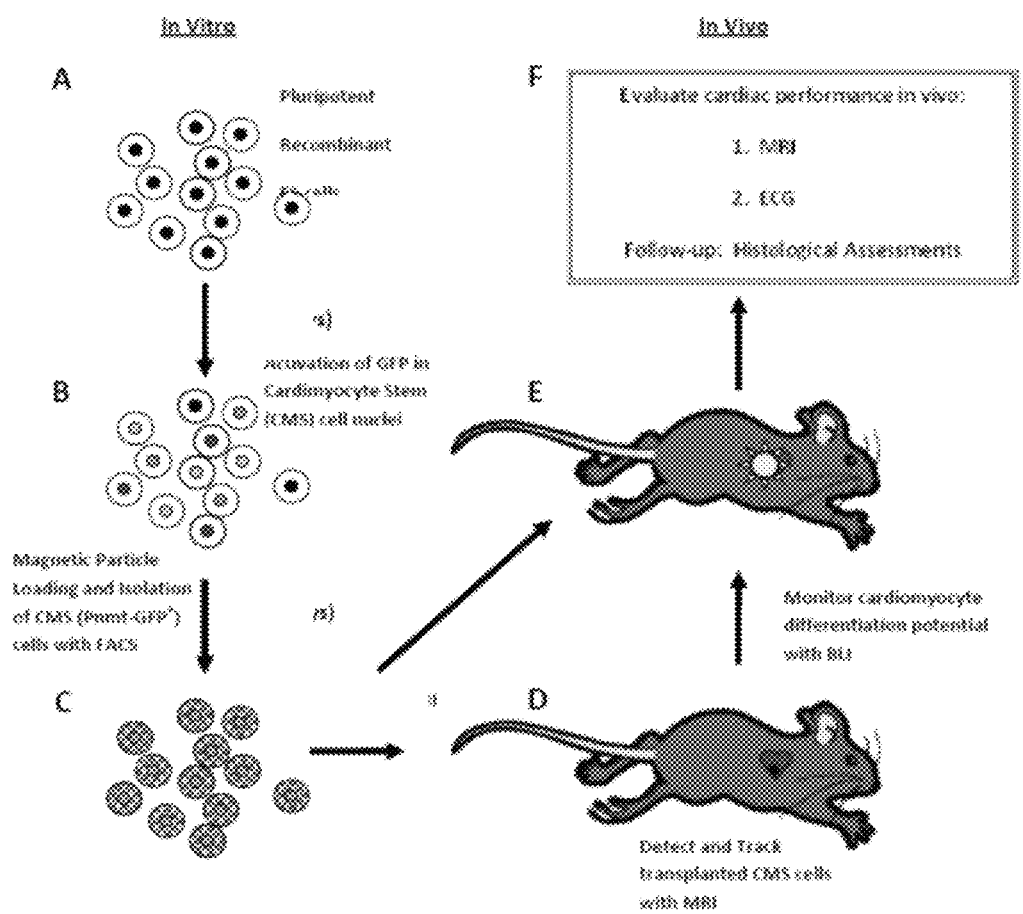
FIGS. 14A-14F are cartoon depictions of a proposed method for molecular imaging. (A) Pluripotent recombinant mouse ES cells (Pnmt-GFP/αMHC-Luc) are expanded in culture, dispersed, and induced to differentiate into beating cardiac cells using the hanging ball method. (B) During the differentiation process, a heterogenous mixture of cells representing various developmental potentials emerges. Applicant has colored the nuclei to represent some of the expected and observed cellular phenotypes: Black=pluripotent stem cell (i.e., undifferentiated, as in 'A'); Grey, cardiac stem (CS) cell (multipotent cell capable of becoming cardiac myocytes, smooth muscle, and endothelial cells (see FIG. 13); Green=cardiomyocyte stem (CMS) cell (identified by Pnmt- EGFP+ expression in nuclei—also see FIG. 17); Red=beating cardiomyocytes. There are other cell types (endothelial, fibroblast, etc.) arising in these cultures, but only a few representative cell types are shown to illustrate the basic idea. (C) While in culture, the cardiac—differentiated cells are loaded with magnetic microsphere particles (for subsequent MRI in vivo) and subjected to fluorescent-activated cell sorting (FACS) to selectively isolate CMS (GFP+) cells loaded with magnetic particles conjugated to a different fluorophore ("Dragon Red"). (D) These isolated CMS cells are then be transplanted into areas of mouse hearts damaged by experimentally-induced myocardial infarction (MI), where they are tracked in vivo over the next several days/weeks using MRI. (E) To determine if the transplanted CMS cells differentiate into cardiomyocytes in vivo, Applicant monitors the mice for activation of the luciferase reporter gene driven from the cardiac α-myosin heavy chain (αMHC) promoter using in vivo bioluminescent imaging (BLI) techniques. (F) Systematic optimization of each step in this process is expected to ultimately lead to successful repair/regeneration of damaged cardiac muscle tissue and significant improvement in cardiac performance (as represented by the Mighty Mouse™ picture).

Applicant's data indicate that cardiac cells transiently expressing the enzyme, Pnmt, ultimately become myocytes that contribute substantially to pacemaking, conduction, and working myocardium. Thus, Pnmt serves as a novel marker of cardiomyocyte progenitor cells (Pnmt+ cells) in the developing heart. Applicant tests the idea that Pnmt+ cells can be selectively isolated and transplanted into damaged cardiac regions where they are monitored both physically (location) and physiologically (function) in vivo using non-invasive molecular and cellular imaging techniques. An exemplary method is shown in FIG. 14. Four specific aims are described as follows:

One aim is to determine the fate of Pnmt+ cells in the heart using newly developed mouse genetic models and "conventional" cellular/molecular imaging techniques (immunofluorescent histochemical staining and confocal laser-scanning fluorescence microscopy). This aim establishes the cellular anatomical distribution pattern of Pnmt+ cells and their descendents in developing mouse hearts.

One experiment is to determine the fate of Pnmt+ cells in the heart using Pnmt-CrexR26R mice. This experiment tests the hypothesis that cardiac Pnmt+ cells differentiate into myocytes in vivo. Applicant has already made substantial progress in this area using the newly developed Pnmt-Cre mice. When bred with R26R reporter mice, Pnmt-Cre activated LacZ expression, thereby allowing Applicant to identify and map descendents of Pnmt+ cells in the developing mouse heart with XGAL staining. Applicant has examined embryonic, fetal, and neonatal hearts. Applicant also examines adult and aged hearts in similar fashion to determine if LacZ+ cells persist and maintain the patterns of distribution noted in the late fetal/early postnatal period. Further, Applicant uses additional cell type-specific markers to determine if Pnmt+ cells differentiate into cells other than myocytes in the heart. This experiment is important for determining the full potential of cardiac Pnmt+ cells in vivo.

Applicant uses dual immunofluorescent and XGAL histochemical staining techniques to identify and map the expression patterns of Pnmt+ cells and their descendents in fixed mouse heart sections. These experiments are performed largely as described above except that additional cell type-specific antibodies are included to determine if Pnmt+ cells give rise to any non-myocyte cell types in the heart. A summary of the representative antibodies that are employed for this analysis is listed in Table 5. Additional cell type-specific antibodies are available for each of the cell types listed. The immunofluorescent staining analyses are performed in conjunction with XGAL histochemical staining. Confocal laser-scanning fluorescence microscopy is used in combination with bright-field microscopy to visualize cellular and subcellular patterns of expression for these markers in the developing heart.

TABLE-US-00005 TABLE 5 Examples of Cell Type-Specific Antibody Markers Available for Co-Staining Experiments. Cell Type Antibody Marker Source References Striated Muscle Sarcomeric α-actinin* Sigma-Aldrich Ebert & (St. Louis, Mo.) Thompson, 2001 Smooth Muscle α-Smooth muscle actin Pacemaker Cells HCN4* Chemicon (SAN and AVN) (Temecula, Calif.) Intrinsic Cardiac PNMT* Chemicon Adrenergic (ICA) Cells (Temecula, Calif.) Cardiac Stem Cells c-Kit* Santa Cruz Biotech (Santa Cruz, Calif.) Epicardial Cells α4-integrin Santa Cruz Biotech (Santa Cruz, Calif.) Endocardial Cells PECAM Cardiac neurons Choline Sigma-Aldrich Acetyltransferase* (St. Louis, Mo.) (ChAT) Fibroblasts Prollagen I *Antibodies that Applicant has tested in published (Ebert & Thompson, 2001; Ferreira et al., 2001) and preliminary studies.

Applicant focuses on three age groups for this experiment: (1) Neonatal (P0-P4); (2) Young Adult (8-10 wks); and Aged (>1.5 yrs). Applicant has already completed most of the prenatal analysis. Most of the work is done with neonates to make the most efficient use of time and resources. The structure of the neonatal heart is similar to that of adults, yet its smaller size means that less reagents (primarily antibodies) are needed to perform this experiment than would be used for adult sections. Applicant has already tested about one-half of the antibodies listed in Table 5 (see asterisks) in neonatal mouse hearts, but Applicant has not yet looked specifically at non-myocyte markers that may identify Pnmt descendents as neuronal, epicardial, endocardial, smooth muscle, or fibroblast cells. Once the staining is done in neonates, more limited testing in adults is performed to determine if the pattern of staining is fundamentally different from that observed in the neonate.

One aspect of adult hearts that is different from neonates is that the development of the intrinsic cardiac nervous system is still immature in neonates, but is fully developed in the adult. Applicant carefully examines LacZ expression in cardiac neurons in adult hearts. As indicated from Table 5, Applicant uses an anti-ChAT antibody as a marker for cholinergic neurons. Another neuronal marker that may be useful is an antibody that recognizes the $α_3$ subunit of the neuronal nicotinic receptor ($α_3$-nAChR). Another method that should prove useful here is silver staining, which selectively identifies neurons. The silver staining technique is relatively inexpensive and easy to perform. It should be relatively straightforward to combine silver staining and XGAL staining in the same sections. Thus, by using these different approaches (immunofluorescent vs. histochemical staining), Applicant is able to determine if Pnmt+ cells become cardiac neurons. The development, function, and regulation of the intrinsic cardiac nervous system are not well understood. Consequently, this experiment could shed new light on this relatively unexplored aspect of cardiac development.

The experiments with the aged hearts is performed primarily to see if there is any loss or attrition of Pnmt$^+$ cell descendents in the heart over time. These experiments are performed on a limited basis unless major differences are noted between aged, adult, and neonatal patterns of LacZ expression in the hearts of these mice.

Based on the published and preliminary data, Pnmt$^+$ cells may primarily give rise to cardiomyocytes. Applicant anticipates that some of these cells may contribute to neural crest derivatives in the heart since the preliminary data suggest that LacZ$^+$ neural crest cells may invade the heart in Pnmt-CrexR26R embryos. Moreover, the Pnmt+ cells that eventually populate the adrenal medulla are known to be derived from migrating neural crest cells. Thus, there is precedence for a neural crest origin of Pnmt+ cells in other tissues, and it is certainly possible that this is also true in the heart. Thus, Applicant carefully examines LacZ expression in these hearts to see if it is consistent with known patterns of neural crest cell distributions in the heart (e.g., outflow tract septum). Since cardiac neurons are also thought to arise from neural crest, Applicant may expect to see some co-staining for LacZ and neuronal markers such as ChAT.

Another experiment is to identify Pnmt$^+$ cells in the heart using Pnmt-nEGFP knock-in mice. To develop a "tag" for living Pnmt$^+$ cells in mice, Applicant has created a new line of Pnmt knock-in mice that express a nuclear-localized Enhanced Green Fluorescent Protein (nEGFP) reporter gene from the endogenous Pnmt gene locus. Applicant hypothesizes that Pnmt$^+$ cells express nEGFP in these mice, and Applicant tests this hypothesis by analyzing fixed tissue sections for nEGFP expression using confocal laser-scanning fluorescence microscopy. The specificity of nEGFP expression in this newly developed model is validated.

Applicant validates the new Pnmt-nEGFP knock-in model by first showing that insertion of the nEGFP reporter effectively disrupted the expression of the endogenous Pnmt gene. Two independent assays are performed to accomplish this goal. First, Applicant measures epinephrine and norepinephrine concentrations in the adrenal glands, heart, and blood from wild-type (Pnmt$^{+/+}$), heterozygous (Pnmt$^{+/nEGFP}$) and homozygous reporter (Pnmt$^{nEGFP/nEGFP}$) mice using a standard radioimmunoassay, as Applicant has described previously (Ebert & Thompson, 2001, supra]. Second, Applicant compares nEGFP expression in various tissues (adrenal glands, heart, etc.) with endogenous Pnmt expression using immunofluorescent histochemical staining methods.

To confirm and extend the findings from the experiments with Pnmt-CrexR26R mice, Applicant examines co-expression of nEGFP with the various cell type-specific antigens listed in Table 5, by using immunofluorescent histochemical staining. nEGFP expression is identified by direct fluorescence emission (green) from the nEGFP reporter protein while co-staining is performed with immunofluorescent histochemical techniques using red fluorescent (Texas Red or TRITC) secondary antibodies.

Applicant expects to find that nEGFP expression is restricted to Pnmt$^+$ cells in vivo, and that homozygous knock-in reporter (Pnmt$^{nEGFP/nEGFP}$) mice do not express endogenous Pnmt or produce epinephrine. In contrast, wild-type (Pnmt$^{+/+}$) and heterozygous (Pnmt$^{+/nEGFP}$) mice are expected to express Pnmt and produce normal levels of epinephrine (as was true for Pnmt-Cre mice). Such results would help to confirm the specificity of the targeted nEGFP insertion into the endogenous Pnmt gene locus as well as the potential usefulness of the nEGFP reporter as a viable marker for Pnmt$^+$ cells. Since Applicant has already demonstrated that another Pnmt knock-in gene, Pnmt-Cre, was expressed specifically as expected in vivo, Applicant expects that nEGFP expression displays a similar pattern of specificity, especially with respect to the ICA cells in the developing heart and the chromaffin cells in the adrenal medulla. Pnmt is normally expressed in limited numbers of cells in various other tissues including brainstem and retinal neurons, lung, spleen, thymus, and testes.

In certain cases, Applicant is able to use the recombinant Pnmt-nEGFP ES cells to generate cardiomyocyte progenitor cells by inducing them to differentiate into beating cardiac cells in vitro. For the purpose of this project, generation of Pnmt-nEGFP mice is not necessary, but would certainly help provide confidence in the fidelity of this targeted reporter gene. In addition, the mice could provide an alternative source of cardiomyocyte stem (Pnmt$^+$) cells (e.g., instead of cardiac-differentiated recombinant ES cells) for the transplantation experiments described for the latter aims. One attractive alternative to Pnmt-nEGFP expression as a reporter would be expression of a unique cell surface marker gene from the Pnmt locus. Applicant could then use fluorescently-tagged antibody strategies to identify the cells and mark them for isolation using FACS. There are many potential marker genes that could be tested as such.

Another aim is to isolate and characterize living cardiac Pnmt$^+$ cells in vitro using fluorescence-activated cell sorting (FACS) and magnetic microsphere particle loading techniques. This aim focuses on optimizing methods for isolating Pnmt$^+$ cells and loading them with magnetic microsphere particles for subsequent transplantation and in vivo imaging analyses.

One experiment is to isolate Pnmt$^+$ cells from cardiac-differentiated Pnmt-nEGFP recombinant ES cells. Applicant plans to take advantage of nEGFP expression from the endogenous Pnmt gene locus to identify and isolate presumptive cardiomyocyte progenitor (Pnmt$^+$) cells from other types of cardiac precursor cells using FACS. This strategy may provide a means to selectively obtain a novel population of cardiomyocyte stem cells that are evaluated in the transplantation experiments described above.

Applicant initiates cardiac differentiation in Pnmt-nEGFP ES cells using the "hanging ball" method. The process takes 7 days to form embryoid bodies that are then transferred to tissue cultureware for attachment. Beating activity develops in the focal adhesion plane over the next few days (e.g., 7+1, 7+2, 7+3 days). Neither the endogenous Pnmt gene nor the Pnmt-nEGFP gene was expressed in undifferentiated ES cells, but both were activated during cardiac differentiation. Endogenous Pnmt mRNA was readily detected at 7+1 and 7+3 days, in strong concurrence with the abundant appearance of nEGFP$^+$ cells at these stages in cardiac-differentiated Pnmt-nEGFP ES cells. These cardiac-differentiated ES cells can be dispersed into single cells using published methods that Applicant has successfully employed. The next step, therefore, is to isolate these cells from non-EGFP$^+$ cells using FACS.

Applicant expects to selectively recover EGFP$^+$ cells from a dispersed population of semi-differentiated ES cells. Although Applicant may ultimately need fewer or more cells for the transplantation experiments, Applicant uses this range (XX-YY) as an initial benchmark for the number of EGFP$^+$ cells needed for each transplantation experiment. Because mouse ES cells can be readily expanded and differentiated in culture, it is not unrealistic to achieve yields in this range.

Indeed, Zandstra et al. [2003] recently demonstrated "Scalable production of ES cell-derived cardiomyocytes" using a similar FACS-based strategy. Thus, it appears feasible to obtain sufficient numbers of cells using this strategy.

Another experiment is to isolate Pnmt$^+$ cells from embryonic mouse hearts (Pnmt-nEGFP mice). A potential limitation of ES cells is that they may differentiate into non-cardiac as well as cardiac cells. Applicant aims to overcome this limitation by selecting Pnmt-nEGFP$^+$ cells from cardiac-differentiated ES cells, but Applicant cannot be certain that all nEGFP$^+$ cells isolated in this manner are cardiac-destined. Indeed, Pnmt is also expressed in neurons, chromaffin cells, and other types of cells that could conceivably "contaminate" the ES cell preparations. To minimize this concern, Applicant also isolates Pnmt-nEGFP$^+$ cells from embryonic/fetal mouse hearts for use in the subsequent transplantation experiments described above.

Applicant uses essentially the same strategy as described for the previous experiment except that Applicant's source material includes embryonic and fetal hearts from transgenic Pnmt-nEGFP knock-in mice. Applicant expects that Pnmt-nEGFP$^+$ cells isolated from embryonic/fetal hearts and cardiac-differentiated ES cells behave similarly in subsequent differentiation and transplantation experiments. By comparing Pnmt-nEGFP$^+$ cells obtained from these two different but related sources, Applicant is able to determine if there are significant differences in the differentiation/transplantation potential of these cell populations.

Another experiment is to perform clonal analysis of Pnmt-nEGFP$^+$ cells. To characterize the differentiation potential of Pnmt-nEGFP$^+$ cells isolated from cardiac-differentiated ES cells and embryonic/fetal hearts, Applicant analyzes clonal colonies of nEGFP$^+$ and non-fluorescent kindred cells obtained during preparation of the cells. Applicant hypothesizes that nEGFP cells differentiate into cardiomyocytes and cease to express nEGFP. By immunofluorescent cytochemical staining of clonal populations with cell type-specific antibody markers (Table 5), the fate of EGFP$^+$ vs. EGFP cells can be determined. This analysis may also provide a means to optimize culture conditions for production of cardiomyocyte stem cells for subsequent transplantation and molecular imaging experiments.

Applicant disperses cardiac-differentiated recombinant Pnmt-nEGFP ES cells and embryonic/fetal mouse hearts carrying the Pnmt-nEGFP knock-in transgene into single-cell suspensions, and culture them at a density of .1toreq.1 cell per well in a 48-well culture dish containing a round glass coverslip. The coverslips be coated with different types of extracellular matrix materials (laminin, collagen, fibronectin, matrigel, etc.) to determine if any of these treatments influences the differentiation and growth potential of the seeded cells. Immediately after seeding, each well is examined and scored for the presence or absence of an EGFP$^+$ or EGFP$^-$ cell by careful (manual) inspection using fluorescence microscopy. Each well is similarly examined on a near-daily basis for 2-3 weeks. Any signs of myocardial development (striations, contractions, etc.) are duly noted. At the end of this visual inspection period, Applicant fixes the cells on the coverslips and subject them to immunofluorescent cytochemical staining using cell type-specific antibodies (Table 5) to determine which cardiac cell types, if any, emerge from this clonal expansion in culture.

Applicant anticipates that at any given stage of cardiac development, there is a heterogeneous mixture of heart-like cells representing many different stages of development and differentiation. Thus, Applicant expects that some nEGFP$^-$ cells may become nEGFP$^+$ if they represent an early stage of cardiac or pre-cardiac stem cells. Conversely, Applicant also expects that some nEGFP$^-$ cells do not differentiate into nEGFP$^+$ cells because they have already proceeded through the cardiomyocyte stem (CMS) cell stage of development or because they have differentiated along a different pathway or not at all. This analysis, while tedious, can be a very powerful tool for determining differentiation potentials of individual cells discriminated by their ability to express nEGFP from the Pnmt gene locus.

Another experiment is to perform magnetic particle-loading of Pnmt-nEGFP$^+$ cells in vitro. To track the position of transplanted cells in vivo using MRI, Applicant pre-loads them with magnetic particles in vitro. Demonstration that Applicant can specifically isolate nEGFP$^+$ cells pre-loaded with magnetic particle beads would set the stage for the transplantation and molecular imaging experiments.

Applicant induces cardiac differentiation in recombinant Pnmt-nEGFP ES cells. After the embryoid bodies are placed onto culture plates (day 7), they are overlaid with polymer-coated magnetic microsphere particles for 24-48 hours. At the end of this incubation period, Applicant removes the media and disperse the cells for FACS isolation. The FACS isolation method can be modified to allow selective isolation of cells that have green fluorescent nuclei (due to nEGFP expression from the Pnmt locus) and red fluorescent cytoplasm (due to the presence of Dragon Red polymer-coated magnetic microsphere particles). A subset of these cells is fixed onto coverslips for photo-documentation of particle loading using dual fluorescence microscopy.

Since these magnetic microsphere particles have been successfully used to pre-load mouse ES cells as well as several other types of cells in culture, Applicant expects that they also effectively pre-load Pnmt-nEGFP$^+$ cells. An obvious potential difficulty is that Pnmt-nEGFP$^+$ cells may not take up the particles efficiently or that Applicant is unable to isolate sufficient numbers of particle-loaded cells to effectively evaluate MRI tracking of these cells once transplanted. It is apparent, however, that if the cells are loaded with the particles, then they are relatively easy to track by MRI. Nevertheless, if Applicant has difficulty loading these cells using the strategy outlined above, Applicant isolates the nEGFP$^+$ cells by FACS first, and then load them with the particles. This would have the advantage of enriching the population of cells to be loaded with the desired type of cells (Pnmt-nEGFP$^+$) for the subsequent transplantation and molecular imaging experiments. Another alternative strategy would be to load the cells with different types of magnetic particles. Optionally, Applicant may simply load cardiac-differentiated cells en masse. Cells pre-loaded with magnetic particles are separated from free particles using Percoll gradients, as previously described.

Another aim is to identify and track cardiac Pnmt$^+$ cells in vivo using magnetic resonance imaging (MRI) techniques following transplantation of these cells into regions of the mouse heart damaged by myocardial infarction (MI) or cryoablation. This aim determines if Pnmt$^+$ cells persist in the heart following transplantation into damaged hearts and if so, whether or not cardiac performance is improved as a result of this intervention.

One experiment is to tracking transplanted cardiomyocyte stem cells using MRI. Applicant hypothesizes that cardiomyocyte stem cells transplanted into damaged regions of the heart facilitate repair and regeneration of the damaged cardiac tissue. Thus, the transplanted cells may remain near the site of transplantation and ultimately contribute to new myocyte formation in the damaged regions. This, in turn, should lead to improved cardiac performance. As a first step towards testing this hypothesis, Applicant identifies and track the location of the transplanted cardiomyocyte stem cells in vivo using MRI.

Cardiomyocyte stem cells (Pnmt-nEGFP$^+$ or similar cells) are pre-loaded and isolated as described above. These cells are delivered to a region of the heart damaged by experimentally-induced myocardial infarction (MI). For controls, Applicant performs mock transplantations and transplantation of non-selected cardiac-differentiated ES cells pre-loaded with magnetic microsphere particles. Applicant performs the transplantations at various times post-MI to determine if there is an optimal window of opportunity for this type of cell-based intervention. In addition, Applicant also varies the number of cells used per transplantation to determine what the optimal number of these cells is for this purpose. In each case, the transplanted cells are identified and tracked in vivo over a period of at least several days, and possibly weeks or months if the cells/signal persists. The MRI results may show that the transplanted cardiomyocyte stem cells remain in the heart at or near the region damaged by the infarction.

One alternative strategy that could prove beneficial here is the use of more localized cryoablation damage rather than MI damage, which can affect a relatively larger portion of the heart. There may be some advantage in trying to repair/regenerate a smaller region of damage. An additional advantage of cryoablation is that Applicant may be able to target more specific areas such as pacemaker myocytes in the SA node. Since Applicant has shown that Pnmt+ cells developmentally contribute to pacemaker myocytes, this would be an attractive model to analyze for this project.

Another experiment is to perform functional assessments of cardiac performance in damaged hearts following transplantation of cardiomyocyte stem cells into the damaged regions in vivo. Applicant hypothesizes that cardiac performance is improved following transplantation of cardiomyocyte stem cells into damaged regions of the heart. Applicant primarily uses MRI to perform these assessments, which can be done in parallel with the MRI tracking experiment described above. Heart rate/rhythmicity and left ventricular ejection fraction is measured as the endpoints for this experiment. Applicant compares cardiac performance in MI mice that received cardiomyocyte stem cell transplants vs. those that did not (mock transplants). Normal (non-MI) littermates serve as an additional control group.

Another experiment is to perform postmortem histological assessment of damaged/repaired cardiac regions. If repair of damaged tissue occurs as a result of cardiomyocyte stem cell transplantations, then Applicant expects to see some evidence of regeneration by examining the damaged region using histological methods. At the termination of the MRI tracking experiment, the mouse is humanely sacrificed and the heart is fixed, processed, and sectioned for histological assessment. To determine the location of the transplanted cells and their descendents (if present), Applicant looks for cells harboring the fluorescent magnetic particles (Dragon Red) that were loaded into the cells prior to transplantation. These assessments are combined with immunofluorescent histochemical staining techniques using cell type-specific antibodies (Table 5) to determine if the transplanted cells differentiated into myocytes or some other type of cardiac cell. In addition, Applicant measures the size of the infarcted region from control and transplanted hearts using morphometric methods.

Applicant expects that the transplanted cells remain in the heart where they predominantly become myocytes. Thus, Applicant expects to find cells that have red fluorescent beads in the cytoplasm (marking transplanted cells and their progeny), with little or no green fluorescence retained in the nuclei of these cells (indicating that Pnmt-nEGFP expression had been shut down during differentiation of the transplanted CMS cells in vivo). Further, if the transplanted cells have differentiated into myocytes, then Applicant expects that cells containing the fluorescent magnetic particles express myocyte-specific markers such as sarcomeric α-actinin. Finally, Applicant expects to see significant thickening of muscle tissue in the infarcted region of hearts receiving transplanted CMS cells relative to control hearts that did not receive transplants.

Another aim is to assess the myocyte differentiation potential of Pnmt$^+$ cells in vivo using bioluminescence imaging (BLI) techniques following transplantation of transgenic myocyte-specific promoter-luciferase reporter cells into regions of the mouse heart damaged by MI or cryoablation. This aim determines if transplanted Pnmt$^+$ cells differentiate into specific types of myocytes in vivo by evaluating luciferase reporter gene expression over time using BLI techniques.

One experiment is to perform bioluminescent imaging of transplanted recombinant ES luciferase reporter cells. The rationale is that if transplanted cardiomyocyte stem cells differentiate into myocytes in vivo, then they should begin to robustly express myocyte-specific genes. This expression can potentially be monitored in vivo using BLI to identify and quantify luciferase reporter expression driven from a strong well-characterized myocyte-specific promoter. Applicant uses the cardiac α-myosin heavy chain (αMHC) promoter fused to a luciferase reporter gene to create a new recombinant ES cell line derived from recombinant Pnmt-nEGFP ES cells. Applicant then tests the resulting stably transfected clones for their ability to express luciferase in undifferentiated vs. cardiac-differentiated ES cells.

Applicant expects that luciferase expression is low or absent in undifferentiated ES cells, but is strongly activated and sustained once the cells differentiate into myocytes. Since Applicant has previously shown that there is an inverse relationship between cardiac Pnmt expression and myocyte-specific expression (Ebert & Thompson, 2001, supra), Applicant also predicts that Pnmt-nEGFP$^+$ cells are not substantially express luciferase, at least until Pnmt promoter activity (and the resulting nEGFP expression) begin to shut down as myocyte differentiation proceeds. Thus, upon transplantation of these recombinant (Pnmt-nEGFP/960 MHC-Luc) ES cells into infarcted or ablated regions of the mouse heart, Applicant expects Pnmt-nEGFP expression to decline and αMHC-Luc to increase as an indicator of myocyte differentiation in vivo.

One alternative would be to transplant ES cells that had already differentiated into myocytes, and hence, would already be expressing high levels of αMHC-Luc. The main difference between this strategy and the primary strategy is that Applicant would not pre-select Pnmt-nEGFP cells by FACS prior to transplantation. In other words, the ES cells are differentiated into beating cardiac cells, dispersed, collected and transplanted en masse into damaged hearts. This should provide a "maximum" luciferase signal from these cells for BLI. If this alternative strategy now permits detection of luciferase activity from the heart in vivo using BLI, then this would suggest that Applicant is primarily dealing with an issue of BLI sensitivity. Applicant also considers using a different myocyte-specific promoter such as cardiac actin or sarcomeric α-actinin.

Another alternative would be to sacrifice the animals at various times post-transplantation, and assay cardiac protein extracts for luciferase activity. Such method would be a powerful and straightforward method for determining if there was any increase in luciferase expression following transplantation. If Applicant observes significant increases in αMHC-Luc activity in these extracts over time, then this would also point to a sensitivity issue for the BLI measurements. If, on the other hand, little or no luciferase activity is produced from transplanted heart extracts, then this would indicate that the transplanted cells are probably not differentiating into myocytes. In either case, these results are supported by the histological assessments described in the previous experiment.

Example 4

Intrinsic Cardiac Catecholamines Help Maintain Beating Activity in Neonatal Rat Cardiomyocyte Cultures
1. Results
To identify ICA cells in neonatal rat hearts, Applicant used immunofluorescent histochemical staining techniques using antibodies that specifically recognize the major catecholamine biosynthetic enzymes. Many brightly labeled fluorescent cells were identified using anti-PNMT antiserum. Co-staining with an anti-TH antibody revealed an essentially identical pattern of expression. These ICA cells were primarily found in the ventricular myocardium near the endocardial surface, but were also observed sporadically throughout the heart. A similar pattern of co-staining was observed when Applicant used anti-DBH and anti-TH antibodies. Positively labeled cells appeared bright, were roundish or triangular in shape, and primarily displayed cytoplasmic staining patterns. Thus, each of the three independent catecholamine biosynthetic enzyme (TH, DBH, and PNMT) antibodies selectively labeled a highly similar subset of cardiac cells in neonatal rat hearts.

To view these presumptive ICA cells in relation to cardiomyocytes, Applicant co-stained sections for PNMT and a myocyte-specific marker, sarcomeric α-actinin. Individual ICA cells were again identified in ventricular myocardium. When co-stained for α-actinin, a characteristic ladder-like sarcomeric pattern was evident in many myocytes. By superimposing the PNMT and α-actinin images, Applicant obtained an "overlay" image where ICA cells can be visualized in direct juxtaposition to underlying myocytes. To identify ICA cells in primary cultures of neonatal rat cardiomyocytes, Applicant seeded the cardiomyocytes onto collagen-coated coverslips and allowed them to develop into synchronous rhythmic beating clusters of cardiomyocytes over a 7-d period. The cells were then fixed and co-immunofluorescently labeled for PNMT and sarcomeric α-actinin. PNMT staining was punctate and cytoplasmic, whereas α-actinin staining was evident in sarcomeric structures. The overlay image shows an ICA cell sitting atop a cluster of cardiomyocytes. ICA cells could also be identified in these cultures by co-staining for DBH and TH. Although the relative abundance of ICA cells in these neonatal rat cardiomyocyte cultures was low (only ~1 ICA cell/$2 \times 10^5$ myocytes), these results nevertheless show that ICA cells were present and that they were closely associated with cardiomyocyte clusters.

Figure 15:
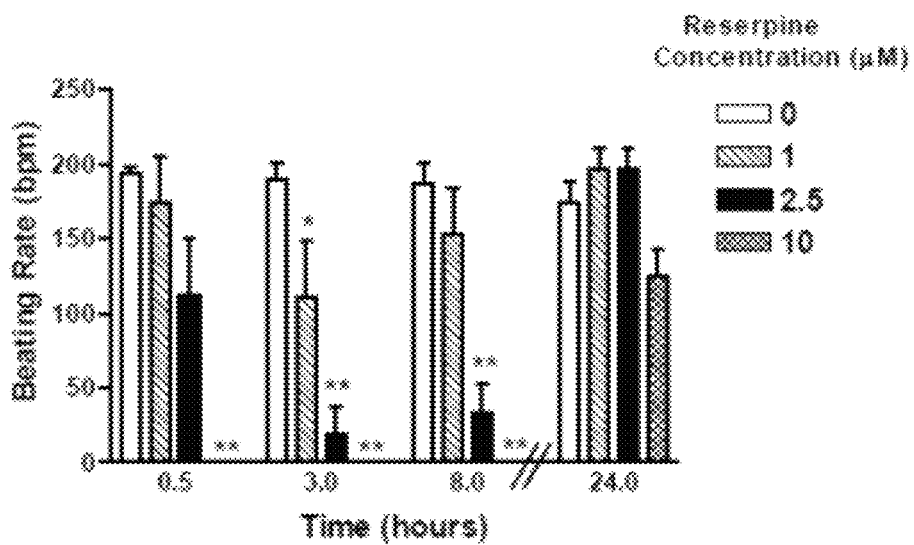
FIGS. 15A-15C show effect of the catecholamine-depleting agent reserpine on the maintenance of beating rate in neonatal rat cardiomyocyte cultures. Spontaneously beating neonatal rat cardiomyocytes were allowed to develop for a period of 7 d in culture, and different concentrations of reserpine were added directly to the culture media in each well, as indicated. (A) Beating rates were measured at the indicated time points in the presence of the indicated concentrations of reserpine (n=6/group). After the measurement at the 8-h time point, the reserpine-containing media was removed (indicated by arrow with designation, "Drug Removal"), the cells were rinsed with drug-free media, and replenished with drug-free growth media. Beating rate measurements were then re-evaluated at the 24-h time point. (B) Sample recording of beating activity after 8 h of reserpine (2.5 µM) treatment in one well. (C) Effect of norepinephrine (NE, 1 µM) on the beating activity of the same cells recorded in pane B approximately 2 min after the addition of NE (before removal or reserpine). Upper trace in panels B and C represents the "event detector signal" used to measure rate. Lower trace in same panels represents the actual photodiode signal. *p<0.05; **p<0.01.
Figure 15:
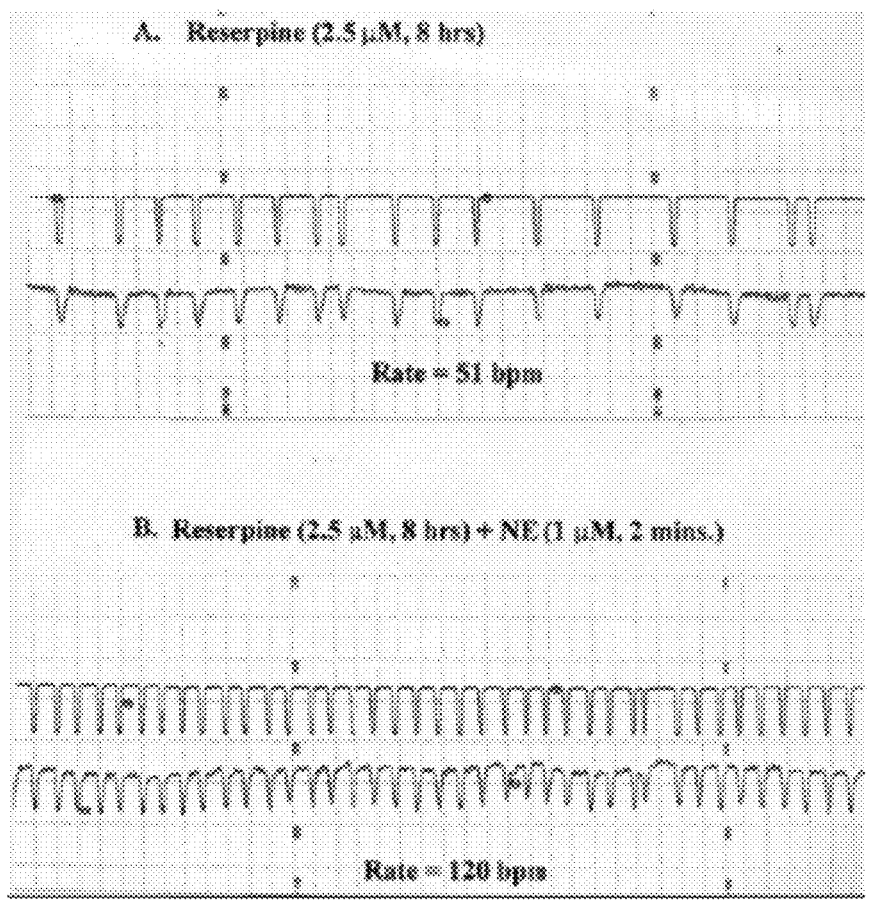

To determine whether beating activity in culture was dependent upon local catecholamine production, the wells were treated with increasing concentrations of reserpine, a catecholamine-depleting agent. Significant dose-dependent decreases in beating rates were observed in the presence of reserpine (FIGS. 15A and B). These decreases could be largely reversed by the addition of norepinephrine (FIG. 15C). These results suggest that endogenous catecholamines are needed for the maintenance of beating rates in these cardiomyocyte cultures.

Figure 16:
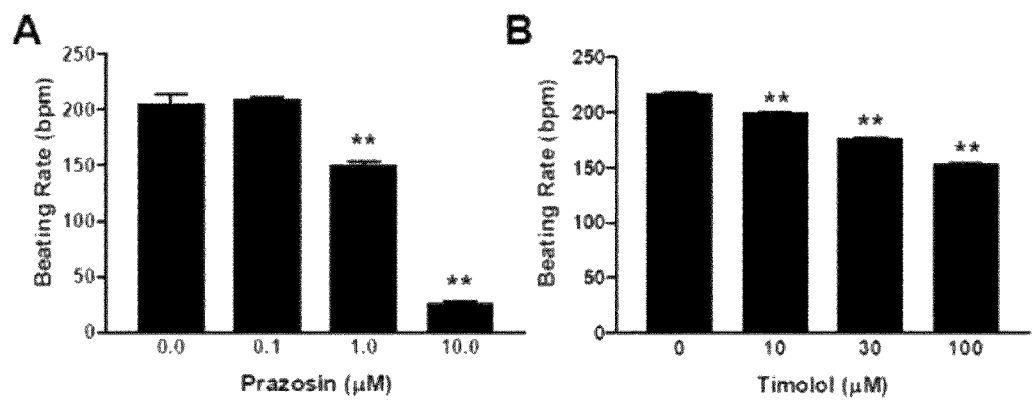
FIGS. 16A-16B show effects of adrenergic antagonists on beating rates in cultured neonatal rat cardiomyocytes. Cardiomyocytes were allowed to develop spontaneous beating activity over a period of 7 d before the addition of drugs. Each drug was added at the indicated concentrations and beating rates were assessed within 1-2 min after drug addition. (A) Effect of increasing concentrations of the $α_1$-selective antagonist prazosin. (B) Effect of increasing concentrations of the β-selective antagonist timolol. **p<0.01 (n=6/group).

Consistent with this idea, acute treatment of spontaneously beating myocyte cultures with either the α1-selective antagonist, prazosin, or the β-selective antagonist, timolol, led to dose-dependent decreases in the beating rate within seconds after drug application (FIG. 16). Significant slowing (~25% decrease) in the beating rate was observed in the presence of 1 µM prazosin (p<0.01, n=10). When the prazosin concentration was increased to 10 µM, severe depression (>85% decrease) in the beating rate occurred. Timolol also caused significant concentration-dependent slowing in the beating rate (p<0.01, n=6). These results show that application of either α1- or β-adrenergic receptor blockers lead to concentration-dependent slowing of beating rate.

Figure 17:
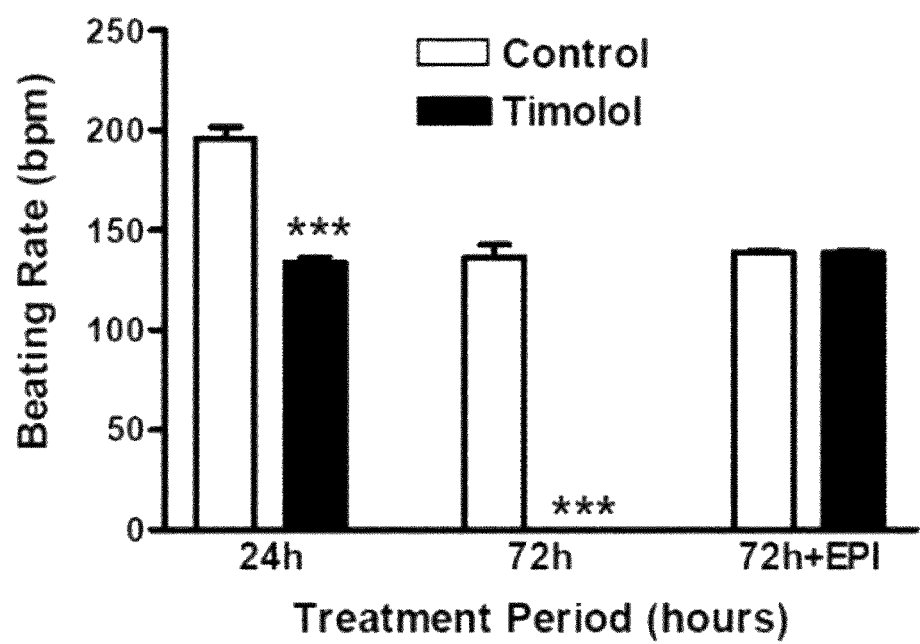
FIG. 17 shows effect of β-adrenergic blockade on beating rates in neonatal rat cardiomyocytes cultured using media containing charcoal-striped serum. Neonatal rat cardiomyocytes were allowed to develop spontaneous beating activity under normal growth conditions for a period of 7 d. On d 7, the culture media was replaced with media containing charcoal-stripped serum to remove any residual catecholamines that may have been present in the serum. Timolol (10 µM) was added to the culture medium containing the charcoal-stripped serum on half of the cultures at the time of media change on d 7. Beating rates were then assessed at 24 and 72 h after drug treatment (cells were cultured in the continuous presence of timolol). Addition of epinephrine (1 µM) enabled full recovery of beating rate for at least 30-60 min. ***p<0.001 relative to control (n=6/group).
Figure 18:
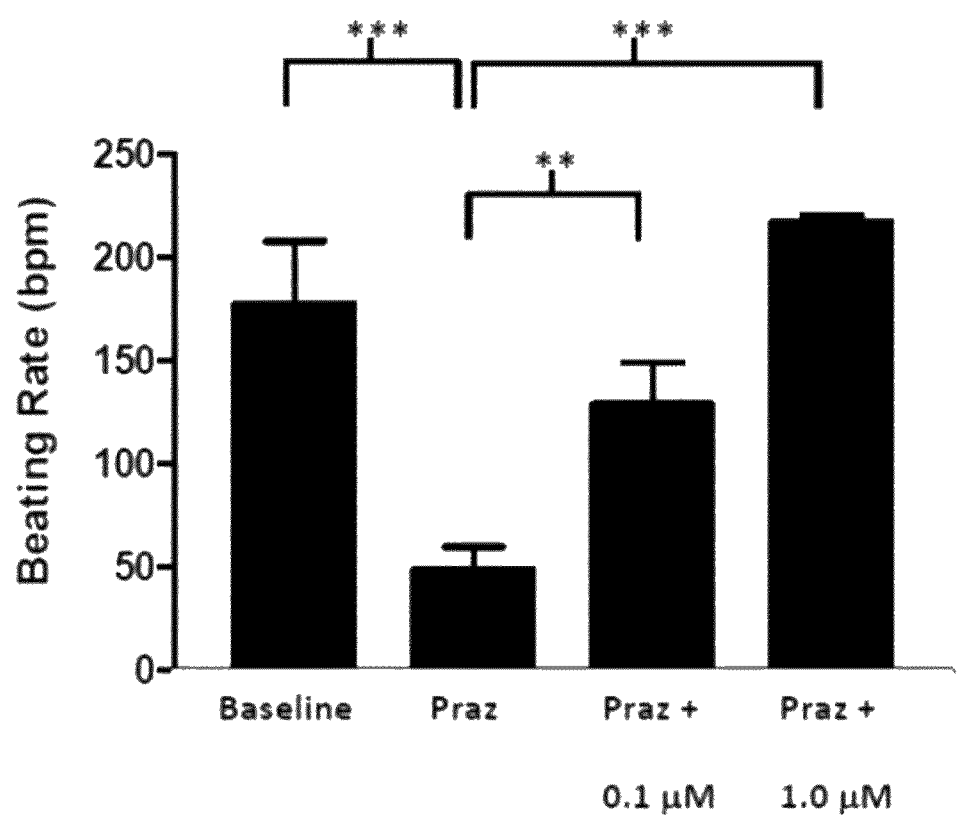
FIG. 18 shows effect of $α_1$-adrenergic blockade on the beating rates in neonatal rat cardiomyocytes cultured in media containing charcoal-stripped serum. Application of the $α_1$-antagonist, prazosin (1 µM) resulted in a significant reduction in the beating rate compared with baseline control. This reduction in the beating rate was reversed by the addition of the $α_1$-agonist, L-phenylephrine (L-PE) at the indicated concentrations. p<0.01; *p<0.001 (n=12/group).

To test the possibility that serum catecholamines may have influenced our results, Applicant stripped the serum using charcoal-treatment to remove any trace amounts of catecholamines that may have been present. Beating activity was maintained for at least 72 h after charcoal-stripping (FIG. 17). The β-blocker timolol strongly suppressed beating activity under these conditions, an effect that was fully rescued by the addition of epinephrine (FIG. 17). Similarly, application of the α1-blocker prazosin led to significant decreases in beating rates (FIG. 18). The addition of the α1-selective agonist, L-phenylephrine, resulted in a dose-dependent reversal of the prazosin-induced decrease in beating rate. These results show that α1- and β-adrenergic receptor antagonists were effective at blocking beating even in the absence of any potential influence from serum catecholamines.

2. Materials and Methods
A) Materials. All drugs and chemicals used for this study were purchased from Sigma Chemical (St. Louis, Mo., U.S.A.). Drugs were prepared as concentrated stock solutions and frozen in small aliquots at –80.degree. C. The stock aliquots were thawed immediately before use and were not refrozen. Rabbit anti-PNMT and anti-DBH antisera have been previously described (3). Mouse monoclonal anti-TH and anti-sarcomeric α-actinin antibodies were purchased from Sigma Chemical. FITC-conjugated donkey anti-rabbit and TRITC-conjugated donkey anti-mouse secondary antibodies were obtained from Jackson Immunoresearch (West Grove, Pa., U.S.A.).

B) Animals. Timed-pregnant Sprague-Dawley rats were obtained from Taconic Farms (Germantown, N.Y., U.S.A.). Neonatal pups were used within the first 2 d after birth. All experiments were conducted in strict concordance with the guidelines provided by the Georgetown University Animal Care and Use Committee and the National Institutes of Health.

C) Immunofluorescent histochemical and cytochemical staining. Double immunofluorescent staining of neonatal rat hearts and cardiomyocyte cultures was performed essentially as described previously (3). For immunofluorescent cytochemical staining of cultured cardiomyocytes, the myocytes were seeded onto collagen-coated coverslips (12 mm round) at the time of isolation, and allowed to grow in culture for 7-9 d before fixation. To fix the cells, the culture medium was removed and the cells were rinsed twice with PBS. The cells were then exposed to 4% paraformaldehyde in PBS for 15 min at room temperature. At the end of this fixation period, the fixative was removed and the cells were washed twice with PBS. The cells were then used immediately for immunofluorescent staining or stored in PBS in 4.degree. C. for subsequent staining.

Because the anti-DBH and anti-PNMT antisera were produced in rabbits while the anti-TH antibody was produced in mice, FITC-conjugated anti-rabbit (green fluorescence) and TRITC-conjugated anti-mouse (red fluorescence) secondary antibodies were used to detect specific labeling of DBH- (or PNMT-) and TH-expressing cells, respectively. Applicant has previously demonstrated the specificity of these antibodies using immunofluorescent histochemical staining assays.

D) Preparation of rat neonatal cardiomyocyte cultures. Neonatal rat cardiomyocytes were prepared according to Simpson and Savion, 1982, Circ Res 50:101-116, with the following modifications: Neonatal rat pups were killed by swift decapitation within the first 2 d after birth. The heart was immediately removed under aseptic conditions and placed in ice-cold sterile HBSS (no $Ca^{++}$ or $Mg^{++}$). Enzymatic and mechanical dissociation of cardiomyocytes was then performed using the Neonatal Cardiomyocyte Isolation System supplied by Worthington Biochemicals (Freehold, N.J., U.S.A.). The hearts were minced on ice and digested overnight at 4.degree. C. with purified trypsin (10 μg/mL) in HBSS. On the following morning, the digested tissue was transferred to a 50-mL conical tube and purified soybean trypsin inhibitor (40 μg/mL) was added to terminate trypsinization. The tissue was oxygenated and warmed to 37.degree. C. Purified collagenase (10 U/mL) was added and digestion proceeded for 45 min at 37.degree. C. with intermittent gentle swirling. Mild trituration was then used to mechanically dissociate the digested tissue, and single-cell suspensions were obtained by filtering this digested material through 70 μm sterile mesh filters. The cells were collected by low-speed centrifugation. The supernatant was discarded and the cell pellet resuspended in DMEM (high glucose, Biofluids, Rockville, Md., U.S.A.) culture medium containing 10% defined iron-supplemented bovine calf serum (Hyclone Laboratories, Logan, Utah, U.S.A.), 2 mM glutamine, and gentamicin sulfate (50 μg/mL). In some experiments, the serum was pretreated with charcoal before adding it to the media (10% volume as above) to remove possible trace amounts of catecholamines that may have been present The cells were then "preplated" to remove fibroblasts, and the remaining cells counted and seeded onto multi-well culture plates at a density of 75,000 cells per $cm^2$. The media was changed every 2-3 d beginning the day after seeding. Bromodeoxyuridine (0.1 mM) was added to the culture media for the first 3 d to further minimize contamination from fibroblasts.

E) Beating rate measurements. Beating activity of cultured cardiomyocytes was measured by edge-detection using photodiode sensors attached to a monitor screen depicting beating cells viewed by videomicroscopy. The entire microscope was enclosed in a temperature-controlled (37.degree. C.), custom-designed incubation chamber (Part numbers: 8400-005, 8506-050, and 8537-025; Coy Laboratory Products, Inc., Grass Lake, Mich., U.S.A.) fed with 5% $CO_2$/95% air to maintain constant pH. The photodiode sensor signal was filtered with an 8-pole Bessel low-pass filter (Model 900CT, Frequency Devices, Inc., Havervill, Mass., U.S.A.) with a cutoff frequency of 1000 Hz, and relayed to a PC equipped with a National Instruments data acquisition board and LabView 4.0 processing software. Parallel outputs were also directed to a Gould TA550 chart recorder and an oscilloscope. Data were continuously acquired and stored to disk for later analysis. Drugs were added and immediately mixed in the media overlying the cells in each well. Predrug (baseline) measurements were performed first, and the indicated drug(s) were added as a 100× stock to the preexisting media on each well, and rapidly mixed. Beating rates were remeasured within 2-3 min after drug addition.

F) Data analysis. The number of beating rate measurements was typically obtained from different wells of multi-well plates (usually six wells per plate), seeded from the same preparation of myocytes. Measurements were obtained immediately before and after the addition of specified drugs. In the reserpine experiment, beating rate measurements were obtained at multiple time-points after drug administration. Each experiment was replicated at least twice using independently isolated cultures, and a representative result from each is shown. Unless otherwise indicated, all beating rate measurements were performed on cells that had been cultured for 7-9 d. All data are expressed as mean.+-.SEM. Statistical significance was assessed by one-way ANOVA, with $p<0.05$ required to reject the null hypothesis. Posthoc testing was performed using Bonferroni's correction for multiple comparisons.

Incorporation by Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. An isolated Phenylethanolamine N-methyltransferase (Pnmt)-positive cardiac progenitor cell, wherein the cardiac progenitor cell is committed to at least one cardiomyocyte specific lineage selected from the group consisting of a pacemaker cell, a His bundle (HIS) cell, a Purkinje fiber (PUR) cell, an atrial working myocyte, and a ventricular working myocyte.

2. The isolated progenitor cell of claim 1, wherein the progenitor cell is positive for a marker selected from the group consisting of c-kit, Sca-1, and MDR1.

3. The isolated progenitor cell of claim 1, wherein the cardiomyoctye is a pacemaker cell selected from the group consisting of a sinoatrial node (SAN) cell and an atrioventricular node (AVN) cell.

4. The isolated progenitor cell of claim 1, wherein the progenitor cell is isolated from a tissue selected from the group consisting of a developing heart and an adult heart.

5. The isolated progenitor cell of claim 1, wherein the progenitor cell is isolated from a cultured stem cell line.

* * * * *

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
caggcgcctc atccctcagc agcc                                          24

<210> SEQ ID NO 2
<211> LENGTH: 24
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 2
ctggccagcg tcggagtcag ggtc                                             24

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtgtacggt cagtaaattg gacaccgtcc tc                                    32
```